(12) United States Patent
Terstappen et al.

(10) Patent No.: US 7,332,288 B2
(45) Date of Patent: Feb. 19, 2008

(54) METHODS AND REAGENTS FOR THE RAPID AND EFFICIENT ISOLATION OF CIRCULATING CANCER CELLS

(75) Inventors: Leon W. M. M. Terstappen, Huntingdon Valley, PA (US); Galla Chandra Rao, Princeton, NJ (US); Jonathan W. Uhr, Dallas, TX (US); Emilian V. Racila, Dallas, TX (US); Paul A. Liberti, Huntingdon Valley, PA (US)

(73) Assignee: Immunivest Corporation, Wilmington, DE (US)

( * ) Notice: Subject to any disclaimer, the term of this patent is extended or adjusted under 35 U.S.C. 154(b) by 257 days.

(21) Appl. No.: 10/269,579

(22) Filed: Oct. 11, 2002

(65) Prior Publication Data

US 2003/0129676 A1    Jul. 10, 2003

Related U.S. Application Data

(60) Continuation of application No. 09/904,472, filed on Jul. 13, 2001, now Pat. No. 6,645,731, which is a division of application No. 09/248,388, filed on Feb. 12, 1999, now Pat. No. 6,365,362.

(60) Provisional application No. 60/110,279, filed on Nov. 30, 1998, provisional application No. 60/110,202, filed on Nov. 30, 1998, provisional application No. 60/074,535, filed on Feb. 12, 1998.

(51) Int. Cl.
| G01N 33/53 | (2006.01) |
|---|---|
| G01N 33/553 | (2006.01) |
| G01N 33/546 | (2006.01) |
| C07K 17/00 | (2006.01) |
| C07K 1/13 | (2006.01) |

(52) U.S. Cl. .................. 435/7.1; 435/7.5; 436/526; 436/533; 530/363; 530/403

(58) Field of Classification Search ................ 435/7.1, 435/7.5; 436/526, 533; 530/363, 403
See application file for complete search history.

(56) References Cited

U.S. PATENT DOCUMENTS

| 3,970,518 | A |   | 7/1976  | Giaever |
|---|---|---|---|---|
| 4,018,886 | A |   | 4/1977  | Giaever |
| 4,230,685 | A | * | 10/1980 | Senyei et al. ............... 436/526 |
| 4,267,234 | A |   | 5/1981  | Rembaum |
| 4,375,407 | A |   | 3/1983  | Kronick |
| 4,452,773 | A |   | 6/1984  | Molday |
| 4,554,088 | A |   | 11/1985 | Whitehead et al. |
| 4,654,267 | A |   | 3/1987  | Ugelstad et al. |
| 4,659,678 | A |   | 4/1987  | Forrest et al. |
| 4,672,040 | A |   | 6/1987  | Josephson |
| 4,775,620 | A |   | 10/1988 | Cardiff et al. |
| 4,795,698 | A | * | 1/1989  | Owen et al. .................... 435/4 |
| 5,186,827 | A |   | 2/1993  | Liberti et al. |
| 5,238,811 | A |   | 8/1993  | Fujiwara et al. |
| 5,466,574 | A |   | 11/1995 | Liberti et al. |
| 5,512,332 | A |   | 4/1996  | Liberti et al. |
| 5,541,072 | A |   | 7/1996  | Wang et al. |
| 5,552,283 | A |   | 9/1996  | Diamandis et al. |
| 5,591,830 | A |   | 1/1997  | Van Aken et al. |
| 5,597,531 | A | * | 1/1997  | Liberti et al. .................. 422/57 |
| 5,660,990 | A | * | 8/1997  | Rao et al. ...................... 435/6 |
| 5,693,539 | A |   | 12/1997 | Miltenyi et al. |
| 5,698,271 | A | * | 12/1997 | Liberti et al. ............... 427/550 |
| 5,714,325 | A |   | 2/1998  | Bianchi |
| 5,876,593 | A |   | 3/1999  | Liberti et al. |
| 5,993,665 | A |   | 11/1999 | Terstappen et al. |
| 6,190,870 | B1 |   | 2/2001  | Schmitz et al. |
| 6,265,229 | B1 |   | 7/2001  | Fodstad et al. |
| 6,365,362 | B1 |   | 4/2002  | Terstappen et al. |

FOREIGN PATENT DOCUMENTS

| WO | WO 9708557 | 3/1997 |
|---|---|---|
| WO | WO 9715597 | 5/1997 |
| WO | WO 0047998 | 8/2000 |

* cited by examiner

*Primary Examiner*—Long V. Le
*Assistant Examiner*—Shafiqul Haq
(74) *Attorney, Agent, or Firm*—Joseph F. Aceto; James L. Wilcox

(57) ABSTRACT

A highly sensitive assay is disclosed which combines immunomagnetic enrichment with multiparameter flow cytometric and immunocytochemical analysis to detect, enumerate and characterize carcinoma cells in the blood. The assay can detect one epithelial cell or less in 1 ml of blood and has a greater sensitivity than conventional PCR or immunohistochemistry by 1-2 orders of magnitude. In addition, the assay facilitates the biological characterization and staging of carcinoma cells.

6 Claims, 8 Drawing Sheets

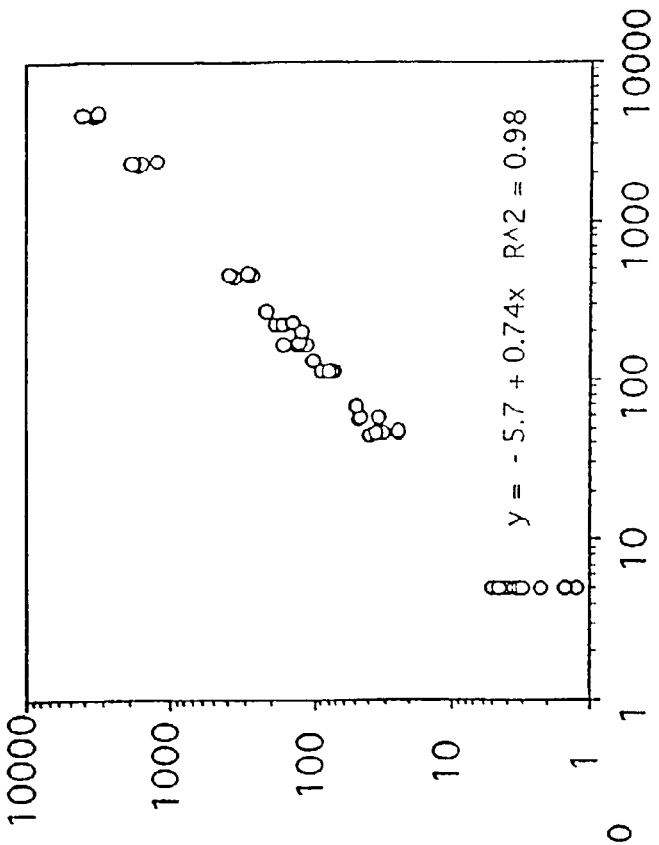
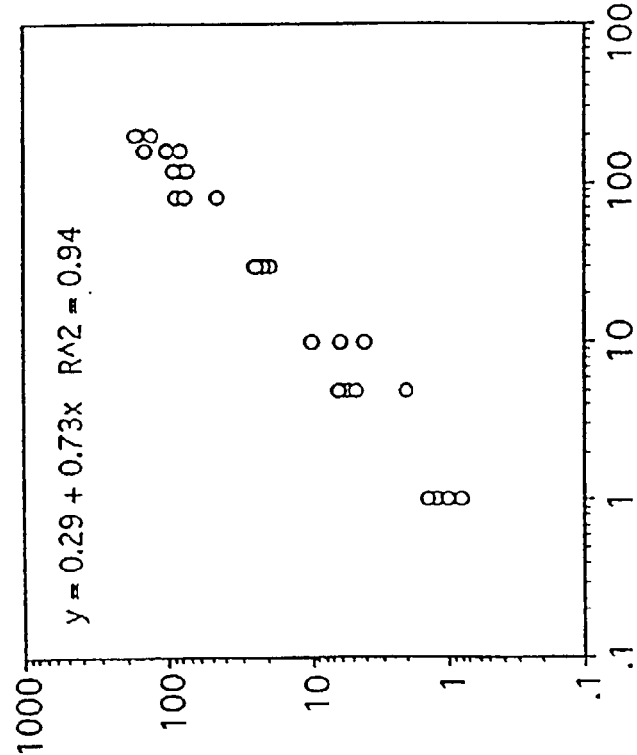
Fig. 1A
Fig. 1B

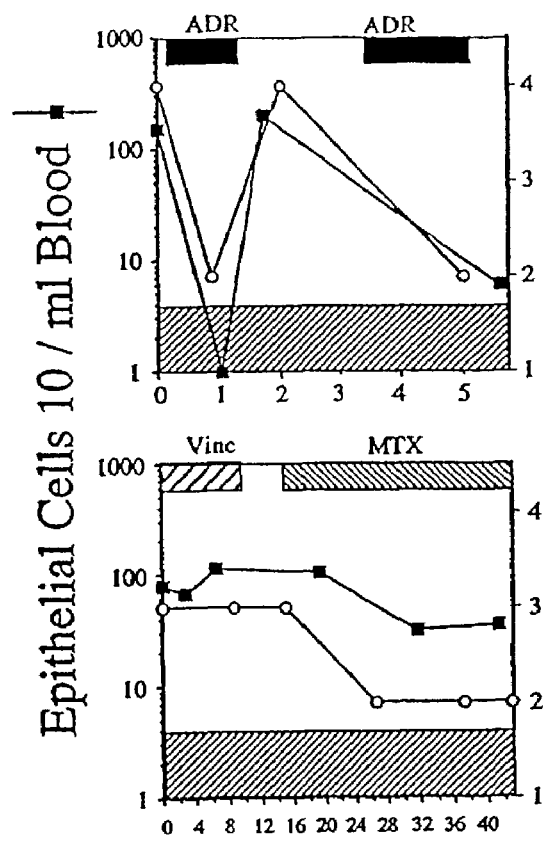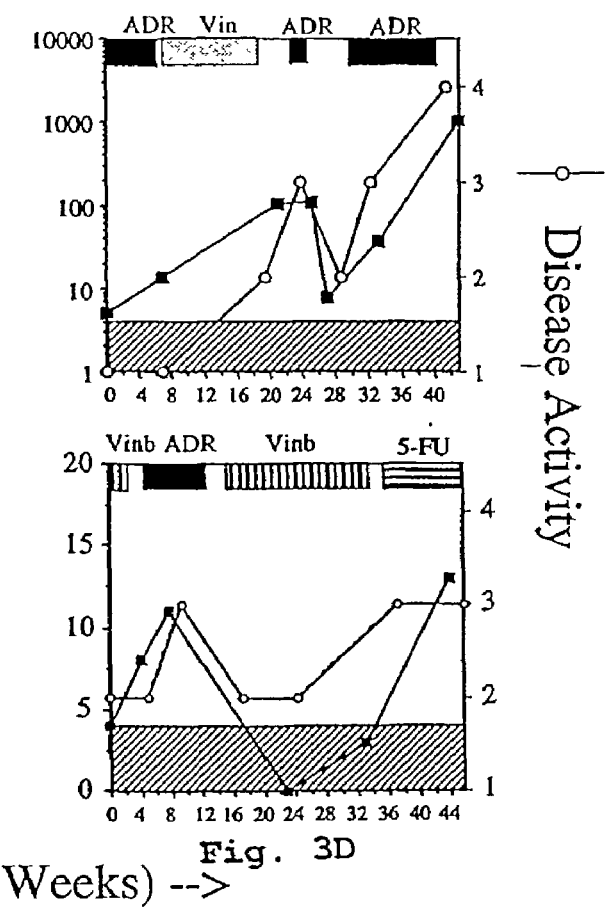
Fig. 3A, Fig. 3B, Fig. 3C, Fig. 3D

Time (Weeks) -->

METHODS AND REAGENTS FOR THE RAPID AND EFFICIENT ISOLATION OF CIRCULATING CANCER CELLS

CONTINUING APPLICATION DATA

This application is a continuation of U.S. application Ser. No. 09/904,472, filed Jul. 13, 2001 now U.S. Pat. No. 6,645,731, which is a divisional application of U.S. application Ser. No. 09/248,388, filed Feb. 12, 1999, now U.S. Pat. No. 6,365,362, which in turn claims priority under 35 U.S.C. §119(e) to U.S. provisional application Nos. 60/074,535, filed Feb. 12, 1998, 60/110,279 and 60/110,202, each filed Nov. 30, 1998. Each of the above identified applications is incorporated by reference herein.

FIELD OF THE INVENTION

This invention relates to the fields of oncology and diagnostic testing. The invention is useful for cancer screening, staging, monitoring for chemotherapy treatment responses, cancer recurrence or the like. More specifically, the present invention provides reagents, methods and test kits which facilitate analysis and enumeration of tumor cells, or other rare cells isolated from biological samples.

BACKGROUND OF THE INVENTION

Each year in the United States, approximately 600,000 new cases of cancer are diagnosed; one out of every five people in this country will die from cancer or from complications associated with its treatment. Considerable efforts are continually directed at improving treatment and diagnosis of this disease.

Most cancer patients are not killed by their primary tumor. They succumb instead to metastases: multiple widespread tumor colonies established by malignant cells that detach themselves from the original tumor and travel through the body, often to distant sites. If a primary tumor is detected early enough, it can often be eliminated by surgery, radiation, or chemotherapy or some combination of those treatments. Unfortunately, the metastatic colonies are harder to detect and eliminate and it is often impossible to treat all of them successfully. Therefore, from a clinical point of view, metastasis can be considered the conclusive event in the natural progression of cancer. Moreover, the ability to metastasize is the property that uniquely characterizes a malignant tumor.

Cancer metastasis comprises a complex series of sequential events. These are: 1) extension from the primary locus into surrounding tissues; 2) penetration into body cavities and vessels; 3) release of tumor cells for transport through the circulatory system to distant sites; 4) reinvasion of tissue at the site of arrest; and 5) adaptation to the new environment so as to promote tumor cell survival, vascularization and tumor growth.

Based on the complexity of cancer and cancer metastasis and the frustration in treating cancer patients over the years, many attempts have been made to develop diagnostic tests to guide treatment and monitor the effects of such treatment on metastasis or relapse. Such tests presumably could also be used for cancer screening, replacing relatively crude tests such as mammography for breast tumors or digital rectal exams for prostate cancers. Towards that goal, a number of tests have been developed over the last 20 years and their benefits evaluated. One of the first attempts was the formulation of an immunoassay for carcinoembryonic antigen [CEA]. This antigen appears on fetal cells and reappears on tumor cells in certain cancers. Extensive efforts have been made to evaluate the usefulness of testing for CEA as well as many other "tumor" antigens, such as PSA, CA 15.3, CA125, PSMA, CA27.29. These efforts have proven to be somewhat futile as the appearance of such antigens in blood have not been generally predictive and are often detected when there is little hope for the patient. In the last few years, however, one test has proven to be useful in the early detection of cancer, viz., Prostate Specific Antigen [PSA] for prostate cancers. When used with follow-up physical examination and biopsy, the PSA test has played a remarkable role in detecting prostate cancer early, at the time when it is best treated.

Despite the success of PSA testing, the test leaves much to be desired. For example, high levels of PSA do not always correlate with cancer nor do they appear to be an indication of the metastatic potential of the tumor. This may be due in part to the fact that PSA is a component of normal prostate tissue as well as other unknown factors. Moreover, it is becoming clear that a large percentage of prostate cancer patients will continue to have localized disease which is not life threatening. Based on the desire to obtain better concordance between those patients with cancers that will metastasize and those that won't, attempts have been made to determine whether or not prostate cells are in the circulation. When added to high PSA levels and biopsy data, the existence of circulating tumor cells might give indications as to how vigorously the patient should be treated.

The approach for determining the presence of circulating prostate tumor cells has been to test for the expression of messenger RNA of PSA in blood. This is being done through the laborious procedure of isolating all of the mRNA from a blood sample and performing reverse transcriptase PCR. As of this date, (Gomella L G. J of Urology. 158:326-337 (1997)) no good correlation exists between the presence of such cells in blood and the ability to predict which patients are in need of vigorous treatment. It is noteworthy that PCR is difficult, if not impossible in many situations, to perform quantitatively, i.e., determine number of tumor cells per unit volume of biological sample. Additionally false positives are often observed using this technique. There is an added drawback which is that there is a finite and practical limit to the sensitivity of this, technique based on the sample size examined. Typically, the test is performed on $10^5$ to $10^6$ cells purified away from interfering red blood cells. This corresponds to a practical lower limit of sensitivity of one tumor cell/0.1 ml of blood. Hence, there needs to be about 10 tumor cells in a ml of blood before signal is detectable. As a further consideration, tumor cells are often genetically unstable. Accordingly, cancer cells having genetic rearrangements and sequence changes may be missed in a PCR assay as the requisite sequence complementarity between PCR primers and target sequences can be lost.

In summary, a useful diagnostic test needs to be very sensitive and reliably quantitative. If a blood test can be developed where the presence of a single tumor cell can be detected in one ml of blood, that would correspond on average to 3000-4000 total cells in circulation. In innoculum studies for establishing tumors in animals, that number of cells can indeed lead to the establishment of a tumor. Further if 3000-4000 circulating cells represents 0.01% of the total cells in a tumor, then it would contain about $4\times10^7$ total cells. A tumor containing that number of cells would not be visible by any technique currently in existence. Hence, if tumor cells are shed in the early stages of cancer, a test with the sensitivity mentioned above would detect the cancer. If tumor cells are shed in some functional relationship with tumor size, then a quantitative test would be beneficial to assessing tumor burden. Heretofore there has been no information regarding the existence of circulating tumor cells in very early cancers. Further, there are very considerable doubts in the medical literature regarding the existence of such cells and the potential of such information. The general view is that tumors are initially well confined and hence there will be few if any circulating cells in early stages of disease. Also, there are doubts that the ability to detect cancer cells early on will give any useful information.

Based on the above, it is apparent that a method for identifying those cells in circulation with metastatic potential prior to establishment of a secondary tumor is highly desirable, particularly early on in the cancer. To appreciate the advantage such a test would have over conventional immunoassays, consider that a highly sensitive immunoassay has a lower limit of functional sensitivity of $10^{-17}$ moles. If one tumor cell can be captured from a ml of blood and analyzed, the number of moles of surface receptor, assuming 100,000 receptors per cell would be $10^{-19}$ moles. Since about 300 molecules can be detected on a cell such an assay would have a functional sensitivity on the order of $10^{-22}$ moles, which is quite remarkable. To achieve that level of sensitivity in the isolation of such rare cells, and to isolate them in a fashion which does not compromise or interfere with their characterization is a formidable task.

Many laboratory and clinical procedures employ biospecific affinity reactions for isolating rare cells from biological samples. Such reactions are commonly employed in diagnostic testing, or for the separation of a wide range of target substances, especially biological entities such as cells, proteins, bacteria, viruses, nucleic acid sequences, and the like.

Various methods are available for analyzing or separating the above-mentioned target substances based upon complex formation between the substance of interest and another substance to which the target substance specifically binds. Separation of complexes from unbound material may be accomplished gravitationally, e.g. by settling, or, alternatively, by centrifugation of finely divided particles or beads coupled to the target substance. If desired, such particles or beads may be made magnetic to facilitate the bound/free separation step. Magnetic particles are well known in the art, as is their use in immune and other bio-specific affinity reactions. See, for example, U.S. Pat. No. 4,554,088 and Immunoassays for Clinical Chemistry, pp. 147-162, Hunter et al. eds., Churchill Livingston, Edinburgh (1983). Generally, any material which facilitates magnetic or gravitational separation may be employed for this purpose. However, it has become clear that magnetic separation means are the method of choice.

Magnetic particles can be classified on the basis of size as large (1.5 to about 50 microns), small (0.7-1.5 microns), or colloidal (<200 nm), which are also referred to as nanoparticles. The latter, which are also known as ferrofluids or ferrofluid-like materials and have many of the properties of classical ferrofluids, are sometimes referred to herein as colloidal, superparamagnetic particles.

Small magnetic particles of the type described above are quite useful in analyses involving bio-specific affinity reactions, as they are conveniently coated with biofunctional polymers (e.g., proteins), provide very high surface areas and give reasonable reaction kinetics. Magnetic particles ranging from 0.7-1.5 microns have been described in the patent literature, including, by way of example, U.S. Pat. Nos. 3,970,518; 4,018,886; 4,230,685; 4,267,234; 4,452, 773; 4,554,088; and 4,659,678. Certain of these particles are disclosed to be useful solid supports for immunological reagents.

Small magnetic particles, such as those mentioned above, generally fall into two broad categories. The first category includes particles that are permanently magnetizable, or ferromagnetic; and the second comprises particles that exhibit bulk magnetic behavior only when subjected to a magnetic field. The latter are referred to as magnetically responsive particles. Materials displaying magnetically responsive behavior are sometimes described as superparamagnetic. However, materials normally considered ferromagnetic, e.g., magnetic iron oxide, may be characterized as superparamagnetic when provided in crystals of about 30 nm or less in diameter. Relatively larger crystals of ferromagnetic materials, by contrast, retain permanent magnet characteristics after exposure to a magnetic field and tend to aggregate thereafter due to strong particle-particle interactions.

Like the small magnetic particles mentioned above, large magnetic particles (>1.5 microns to about 50 microns) can also exhibit superparamagnetic behavior. Typical of such materials are those described by Ugelstad in U.S. Pat. No. 4,654,267 and manufactured by Dynal, (Oslo, Norway). The Ugelstad process involves the synthesis of polymer particles which are caused to swell and magnetite crystals are embedded in the swelled particles. Other materials in the same size range are prepared by synthesizing the polymer particle in the presence of dispersed magnetite crystals. This results in the trapping of magnetite crystals in a polymer matrix, thus making the resultant materials magnetic. In both cases, the resultant particles have superparamagnetic behavior, which is manifested by the ability to disperse readily upon removal of the magnetic field. Unlike magnetic colloids or nanoparticles previously referred to and discussed in further detail below, these materials, as well as small magnetic particles, are readily separated with simple laboratory magnetics because of the mass of magnetic material per particle. Thus, separations are effected in gradients from as low as a few hundred gauss/cm on up to about 1.5 kilogauss/cm. Colloidal magnetic particles, (below approximately 200 nm), on the other hand, require substantially higher magnetic gradients because of their diffusion energy, small magnetic mass per particle and Stokes drag.

U.S. Pat. No. 4,795,698 to Owen et al. relates to polymer-coated, colloidal, superparamagnetic particles which are produced by the formation of magnetite from $Fe^{+2}/Fe^{+3}$ salts in the presence of polymer. U.S. Pat. No. 4,452,773 to Molday describes a material similar in properties to those described in Owen et al., which is produced by forming magnetite and other iron oxides from $Fe^{+2}/Fe^{+3}$ via base addition in the presence of very high concentrations of dextran. The resulting particles from both procedures exhibit an appreciable tendency not to settle from aqueous suspensions for observation periods as long as several months. Materials so produced have colloidal properties and have proved to be very useful in cell separation. The Molday technology has been commercialized by Miltenyi Biotec, Bergisch Gladbach, Germany and Terry Thomas, Vancouver, Canada.

Another method for producing superparamagnetic, colloidal particles is described in U.S. Pat. No. 5,597,531. In contrast to the particles described in the Owen et al., or Molday patents, these latter particles are produced by directly coating a biofunctional polymer onto pre-formed superparamagnetic crystals which have been dispersed by high power sonic energy into quasi-stable crystalline clusters ranging from 25 to 120 nm. The resulting particles, referred to herein as direct-coated particles, exhibit a significantly larger magnetic moment than colloidal particles of the same overall size, such as those described by Molday or Owen et al.

Magnetic separation techniques are known wherein a magnetic field is applied to a fluid medium in order to separate ferromagnetic bodies from the fluid medium. In contrast, the tendency of colloidal, superparamagnetic particles to remain in suspension, in conjunction with their relatively weak magnetic responsiveness, requires the use of high-gradient magnetic separation (HGMS) techniques in order to separate such particles from a non-magnetic fluid medium in which they are suspended. In HGMS systems, the gradient of the magnetic field, i.e., the spatial derivative, exerts a greater influence upon the behavior of the suspended particles than is exerted by the strength of the field at a given point.

HGMS systems can be divided into two broad categories. One such category includes magnetic separation systems which employ a magnetic circuit that is entirely situated externally to a separation chamber or vessel. Examples of such external separators are described in U.S. Pat. No. 5,186,827 to Liberti et al. In several of the embodiments described in this patent, the requisite magnetic field gradient is produced by positioning permanent magnets around the periphery of a non-magnetic container such that the like poles of the magnets are in a field-opposing configuration. The extent of the magnetic field gradient within the test medium that may be obtained in such a system is limited by the strength of the magnets and the separation distance between the magnets. Hence, there is a finite limit to gradients that can be obtained with external gradient systems.

Another type of HGMS separator utilizes a ferromagnetic collection structure that is disposed within the test medium in order to 1) intensify an applied magnetic field and 2) produce a magnetic field gradient within the test medium. In one known type of internal HGMS system, fine steel wool or gauze is packed within a column that is situated adjacent to a magnet. The applied magnetic field is concentrated in the vicinity of the steel wires so that suspended magnetic particles will be attracted toward, and adhere to, the surfaces of the wires. The gradient produced on such wires is inversely proportional to the wire diameter, such that magnetic reach decreases with increasing diameter. Hence, very high gradients can be generated.

One drawback of internal gradient systems is that the use of steel wool, gauze material, or steel microbeads, may entrap non-magnetic components of the test medium by capillary action in the vicinity of intersecting wires or within interstices between intersecting wires. Various coating procedures have been applied to such internal gradient columns (see, e.g., U.S. Pat. No. 5,693,539 to Miltenyi and U.S. Pat. No. 4,375,407 to Kronick), however, the large surface area in such systems still creates recovery concerns due to adsorption. Hence, internal gradient systems are not desirable, particularly when recovery of very low frequency captured entities is the goal of the separation. Furthermore, they make automation difficult and costly. Both the materials described by Owen et al., and Molday require the use of such high gradient columns.

In contrast, HGMS approaches using external gradients for cell separation provide a number of conveniences. Firstly, simple laboratory containers such as test tubes, centrifuge tubes or even vacutainers (used for blood collection) can be employed. When external gradients are of the kind that produce monolayers of separated cells, as is the case with quadrupole/hexapole devices of the above-mentioned U.S. Pat. No. 5,186,827 or the opposing dipole arrangement described in U.S. Pat. No. 5,466,574 to Liberti et al., washing of cells or subsequent manipulations are facilitated. Further, recoveries of cells from tubes or similar containers is a simple and efficient process. This is particularly the case when compared to recoveries from high gradient columns. Such separation vessels also provide another important feature, which is the ability to reduce sample volume. For example, if a particular human blood cell subset, (e.g. magnetically labeled CD $34^+$ cells), is isolated from a 10 ml blood sample diluted 50% with buffer to reduce viscosity, a 15 ml conical test tube may be employed as the separation vessel in an appropriate quadrupole magnetic device. Starting with 15 mls of solution, a first separation is performed, and the recovered cells are resuspended in 3 mls. A second wash/separation is then performed and the isolated cells resuspended in a final volume of 200 ul. After the washes and/or separations and resuspensions to remove non-bound cells, CD $34^+$ cells can effectively be resuspended in a volume of 200 μl. When done carefully in appropriately treated vessels using direct-coated ferrofluids which have been optimized for these separators, cell recovery is quite efficient in the 40-90% range depending on antigen density. Such techniques and reagents are essential to achieve the degree of sensitivity required for the kinds of cancer testing mentioned above.

The efficiency with which magnetic separations can be done and the recovery and purity of magnetically labeled cells will depend on many factors. These include such considerations as the number of cells being separated, the receptor density of such cells, the magnetic load per cell, the non-specific binding (NSB) of the magnetic material, the technique employed, the nature of the vessel, the nature of the vessel surface, the viscosity of the medium and the magnetic separation device employed. If the level of non-specific binding of a system is substantially constant, as is usually the case, then as the target population decreases so will the purity. As an example, a system with 0.8% NSB that recovers 80% of a population which is at 0.25% in the original mixture will have a purity of 25%. Whereas, if the initial population was at 0.01% (one target cell in $10^6$ bystander cells), and if the NSB were 0.001%, then the purity would be 8%. The greater the purity, the easier and better the analysis. Hence, it is clear that extremely low non specific binding is required to perform meaningful rare cell analysis.

Less obvious is the fact that the smaller the population of a targeted cell, the more difficult it will be to magnetically label and to recover. Furthermore, labeling and recovery will markedly depend on the nature of magnetic particle employed. For example, when cells are incubated with large magnetic particles, such as Dynal beads, cells are labeled through collisions created by mixing of the system, as the beads are too large to diffuse effectively. Thus, if a cell were present in a population at a frequency of 1 cell per ml of blood or even less, as may be the case for tumor cells in very early cancers, then the probability of labeling target cells will be related to the number of magnetic particles added to the system and the length of time of mixing. Since mixing of cells with such particles for substantial periods of time would be deleterious, it becomes necessary to increase particle concentration as much a possible. There is, however, a limit to the quantity of magnetic particle that can be added, as one can substitute a rare cell mixed in with other blood cells for a rare cell mixed in with large quantities of magnetic particles upon separation. The latter condition does not markedly improve the ability to enumerate the cells of interest or to examine them.

There is another drawback to the use of large particles to isolate cells in rare frequencies (1 to 50 cells per ml of blood). Despite the fact that large magnetic particles allow the use of external gradients of very simple design and relatively low magnetic gradient, large particles tend to cluster around cells in a cage-like fashion making the cells difficult to see or to analyze. Hence, the magnetic particles must be released from the target cells before analysis, and releasing the particles clearly introduces other complications.

Based on the foregoing, high gradient magnetic separation with an external field device employing highly magnetic, low non-specific binding, colloidal magnetic particles is the method of choice for separating a cell subset of interest from a mixed population of eukaryotic cells, particularly if the subset of interest comprises but a small fraction of the entire population. Such materials, because of their diffusive properties, readily find and magnetically label rare events, such as tumor cells in blood. Such separation generally relies upon the identification of cell surface antigens that are unique to a specific cell subset of interest, which in the case of tumor cells, can be tumor antigens to which appropriate monoclonal antibody conjugated ferrofluids can be targeted. Alternatively, when examining a blood sample, determinants on classes of cells such as epithelial cells, which are normally not found in blood, can provide an appropriate receptor.

There are other good reasons to employ a colloidal magnetic material for such separations, providing an appropriate magnetic loading can be achieved. With appropriate loading, a sufficient force is exerted on a cell such that isolation can be achieved even in a media as viscous as that of moderately diluted whole blood. As noted, colloidal magnetic materials below about 200 nanometers will exhibit Brownian motion which markedly enhances their ability to collide with and magnetically label rare cells. This is demonstrated in U.S. Pat. No. 5,541,072 where results of very efficient tumor cell purging experiments are described employing colloidal magnetic particles or ferrofluids having a mean diameter of 100 nm. Just as importantly, colloidal materials having a particle size at or below this size range do not generally interfere with examination of cells. Cells so retrieved can be examined by flow cytometry, laser scanning microscopy, or by microscopy employing visible or fluorescent techniques.

SUMMARY OF THE INVENTION

The present invention is based on several important discoveries which have significant clinical ramifications for the diagnosis and treatment of cancer. These are 1) tumor cells are present in the blood of patients considered to have clinically localized, primary tumors; 2) the number of tumor cells present in the circulation is correlatable with all stages of cancer from its inception to its terminal stages; and 3) changes in the number of tumor cells present in the circulation is indicative of disease progression. A decrease in the numbers of circulating tumor cells is indicative of improvement in patient status or efficacy of treatment, whereas an increase indicates a worsening of the disease.

The present invention provides a rapid and efficient screening method for the characterization of not only tumor cells, but also rare cells, or other biological entities from biological samples. The method of the invention provides highly sensitive analytical techniques which enable efficient enrichment for entities of interest. This two stage methodology which ensures enrichment of target bioentities while eliminating a substantial amount of debris and other interfering substances prior to analysis, allows for examination of sample sizes which would otherwise be impractical. The method described herein combines elements of immunomagnetic enrichment with multiparameter flow cytometric, microscopic and immunocytochemical analysis in a unique way. Other means of enrichment such as density gradient centrifugation or panning or alteration of target cell density by appropriate labeling may also be utilized. According to a preferred embodiment, the method of the invention enables assaying whole blood for cancer staging, monitoring and screening. The sensitive nature of the assay facilitates the detection of residual disease, thus making it possible to monitor for cancer recurrence.

In one embodiment of the invention, a biological specimen, which comprises a mixed cell population suspected of containing the rare cell of interest is obtained from a patient. An immunomagnetic sample is then prepared by mixing the biological specimen with i. magnetic particles which are coupled to a biospecific ligand specifically reactive with a rare cell determinant or a class of determinants different than those found on blood cells, to the substantial exclusion of other sample components, and ii. at least one biospecific reagent which labels rare cells. The resulting immunomagnetic sample is subjected to a magnetic field which is effective to separate the sample into an unlabeled fraction and a labeled, magnetic fraction including the rare cell of interest, if any is present in the specimen. The cell population so isolated is then analyzed to determine the presence and number of rare cells. In a preferred embodiment the particles used in this method are colloidal nanoparticles.

In another embodiment of the invention, a biological specimen is obtained from a patient. An immunomagnetic sample is then prepared wherein the biological specimen is mixed with colloidal magnetic particles which have been coupled to a monoclonal antibody reactive with the rare cell determinant or a class of determinants different than those found on blood cells. As an alternative to monoclonal antibodies, single chain or engineered fragments of antibodies may be employed. The preparation is subjected to a magnetic field, enriching the rare cell component of the specimen. A second set of monoclonal antibodies, labeled with reporter molecules, are added to the sample and the cells are again magnetically separated in order to remove unbound reagent to lower background staining. A nucleic acid dye or other reporter molecule capable of identifying objects as cells, also referred to herein as a cell specific dye, is added to the sample to allow exclusion of any residual non-nucleated cells or other sample components prior to analysis by flowcytometry, microscopy, or other analytical platforms. Cell specific dyes may be reactive with DNA, RNA, protein, or lipids such that the amount of signal obtained is typical for that obtained for cells or the image obtained reveals typical features of a cell, such as cell and nuclear membranes, nucleus, and mitochondria.

In a further embodiment of the invention, the isolated cells are subjected to immunocytochemical analysis by flowcytometry or other analytical platforms. Such analysis facilitates diagnosis and provides important information to the clinician.

The method of the invention may be used to assess residual cancer cells in circulation following medical, radiation, or surgical treatment to eradicate the tumor. The method may be also be performed periodically over a course of years to assess the patient for the presence and number of tumor cells in the circulation as an indicator of occurrence, recurrence and/or progression of disease.

In yet another aspect of the present invention, a coated, magnetic particle is provided which comprises a nanoparticle core of magnetic material, and a base coating material on the magnetic core in an amount sufficient to hinder non-specific binding of biological macromolecules to the magnetic core. These magnetic particles are characterized by extremely low non-specific binding as well as highly efficient target capture which are essential to achieve a level of enrichment the enrichment required to effectively isolate very rare cells. In an alternative embodiment, a coated, magnetic particle is provided which comprises the following: i. a nanoparticle core of magnetic material; ii. a base coating material that forms a discontinous coating on the magnetic core, providing at least one area of discontinuity which, if accessible, contributes to non-specific binding of the base coated particle to biological macromolecules; and iii. an additional coating material that hinders access to the areas of discontinuity by biological macromolecules. The magnetic core material of the particles described immediately above may comprise at least one transition metal oxide and a suitable base coating material comprises a protein. Proteins suitable for coating magnetic particles include but are not limited to bovine serum albumin and casein. The additional coating material may be the original coating proteins or one member of a specific binding pair which is coupled to the base material on the magnetic core. Exemplary specific binding pairs include biotin-streptavidin, antigen-antibody, receptor-hormone, receptor-ligand, agonist-antagonist, lectin-carbohydrate, Protein A-antibody Fc, and avidin-biotin. In one embodiment, the member of the specific binding pair is coupled to the base coating material through a bifunctional linking compound. Exemplary biofunctional linking compounds include succinimidyl-propiono-dithiopyridine (SPDP), and sulfosuccinimidil-4-[maleimidomethyl]cyclohexane-1-carboxylate (SMCC), however a variety of other such heterobifunctional linker compounds are available from Pierce, Rockford, Ill.

The coated magnetic particles of the invention preferably have between 70-90% magnetic mass. In a preferred embodiment, a major portion of the magnetic particles have a particle size in the range of 90-150 nm. Particles may be synthesized such that they are more monodisperse, e.g., in the range of 90-120 nm or 120-150 nm. The particles of the invention are typically suspended in a biologically compatible medium.

In a further aspect of the present invention, a test kit is provided for screening a patient sample for the presence of circulating rare cells. The screening kit comprises:
i. coated, magnetic nanoparticles coupled, directly or indirectly, to a biospecific ligand that has affinity for a first characteristic determinant on a rare cell;
ii. at least one biospecific reagent having binding specificity for a second characteristic determinant present on a rare cell; and iii. a cell specific dye for excluding other non-target or sample entities from analysis.

In a particularly preferred embodiment, a kit is provided for screening biological samples for circulating cancer cells. The screening kit comprises:
i. coated, magnetic nanoparticles coupled, directly or indirectly to a biospecific ligand that has affinity for a first characteristic determinant on a cancer cell;
ii. at least one biospecific reagent having binding specificity for a second characteristic determinant present on a cancer cell; and iii. a cell specific dye for excluding non-target entities from analysis. The kits provided herein may further include an antibody which has affinity for non-rare, or non-tumor cells, a biological buffer, a permabilization buffer, a protocol and, if desired, an information sheet. In a preferred embodiment, the colloidal magnetic particles are conjugated to anti-EpCAM (an antibody having binding specificity for epithelial cell adhesion molecule), the biospecific reagents comprise a panel of monoclonal antibodies and the cell specific dye stains nucleic acids.

The kits of the invention may contain reagents for diagnosing the type of the metastatic cancer cells in the circulation as well as the metastatic potential and aggressiveness of such cells. In this embodiment the kit contains the reagents recited above, yet also comprises additional antibody markers to facilitate cancer diagnosis. Using breast cancer as an example, such antibodies may include anti-MUC-1, anti-estrogen receptor, anti-progesterone receptor, anti-CA27.29, anti-CA15.5, anti-cathepsin D, anti-p53, anti-urokinase type plasminogen activator, anti-epidermal growth factor, anti-epidermal growth factor receptor, anti-BRCA1, anti-BRCA2, anti-prostate specific antigen, anti-plasminogen activator inhibitor and/or anti-Her2-neu antibodies. Additional markers for aggressiveness and invasiveness are Lewis a (Lea), sialyl Lewis a (sLea), the intergrins (CD49b, CD49c, CD29), gelatinase A and B (MMP-2, MMP-9), tissue collagenase (MMP-1), fibroblast activation protein (FAP), guanidinobenzoatase, CEA, S100 family (S100A4, mtsl, 18A2/mtsl, pEL-98, p9Ka, metastasin), the Cyclins A and E, p27, p53, vascular endothelilal growth factor (VGEF) and E-Cadherin.

In yet another embodiment of the invention, a test kit is provided for monitoring a patient for recurrence of the cancer, and/or response to therapy. This particular kit may also be used to assess high risk patients for the presence of particular tumor cells in the blood. A kit suitable for monitoring a patient would include containers, colloidal magnetic particles conjugated to anti-EpCAM, at least one monoclonal antibody specific for the particular cancer cells for which the patient is being monitored and a fluorescent reporter molecule which can identify the objects as cells, such as nucleic acid or membrane dyes. A kit suitable for monitoring breast cancer patients comprises an antibody having binding affinity for a particular breast cancer marker, for example Her-2-neu. The kits described above are suitable for screening, diagnosing and monitoring patients for breast cancer. It will be appreciated by those skilled in the art that many different cancers may be screened, diagnosed and monitored according to the present invention simply by varying the antibodies provided in the test kit. For example, if a test subject were being assessed for the presence of prostate cancer, antibodies specific for prostate specific antigen may be employed. Other markers for prostate cancer include prostatic acid phosphatase, creatine kinase, thymosin b-15, p53, HPC1 basic prostate gene, and prostate specific membrane antigen.

There is general agreement that the hallmark of successful treatment of cancer is early diagnosis. Based on the data presented herein, it appears that the blood test of the present invention may be used to screen the blood of patients who do not have a diagnosis of cancer, in order to detect cancer earlier than is possible using other existing methods. Such patients may include those with a family history of certain cancers, patients with certain mutations known to be associated with cancer, etc.

Since cancer cells invade surrounding tissue and breakdown tissue barriers, we hypothesize that tumor cells enter the tissue space and capillaries to eventually end up in the blood very early in the development of a solid tumor, i.e., when the tumor contains $10^4$-$10^6$ tumor cells. See FIG. 8. At that point in time, the tumor cells undergo apoptotic cell death, or become dormant because they are not yet able to survive or grow, respectively, in an ectopic environment. There are no techniques at present to detect such small primary tumors. There are sensitive techniques that are available for detecting certain types of cancer when the tumors are larger. For example, mammography can detect $2 \times 10^8$ breast cancer cells at best. More often, tumors of the breast are detected when there are between $5 \times 10^8$ to $10^9$ tumor cells. At this early stage, we hypothesize that most shed tumor cells will die. However, during the many generations that occur as a tumor grows between $10^6$ to $10^{8-9}$ tumor cells, the genetically unstable clone of tumor cells undergoes further genetic changes giving rise to more rapidly growing and aggressive mutant cells. It is very likely these cells that go on to establish secondary tumors. However, in the majority of tumors, the diagnosis is made very late, e.g., pancreas, stomach, ovary, kidney, lung, colon, etc., are usually diagnosed when there are $10^{10}$-$10^{12}$ tumor cells. By this time the tumor has frequently invaded surrounding tissues and/or has metastasized. In light of the foregoing, it is clear that any test which would effectively detect circulating cancer cells prior to the establishment of a secondary tumor would be extremely beneficial in the diagnosis and treatment of cancer. The blood test described herein enables such detection.

BRIEF DESCRIPTION OF THE DRAWINGS

FIGS. 1A and 1B shows the results of model experiments in which known number of tumor cells are spiked into peripheral blood and retrieved after immunomagnetic selection and analysis by either microscopy (FIG. 1A) or flowcytometry (FIG. 1B).

FIGS. 3A-3H shows epithelial cell number in 10 ml of blood and clinical activity of the disease at different time points for eight patients with active carcinoma of the breast. The clinical activity of the disease was classified in categories 1 through 4, as set out in Table 1. The bars at the top represent the length of time of chemotherapy. FIG. 1A, adriamycine (ADR) 90 and 110 mg/m² respectively, FIG. 1B, ADR 30 mg/m²/week, Vinorelbine (Vin) 20 mg/m²/week, ADR 160 mg, ADR 20 mg/m²/week, FIG. 1C, vincristine (Vinc) 0.7 mg/m²/week, metotrexate (MTX) 30 mg/m²/week, FIG. 1D, vinblastine (Vinb) 7 mg/m²/week, ADR 20 mg/m²/week, Vinb 6 mg/m²/week, 5-fluoruracil (5FU) 700 mg/m²/week, FIG. 1E, Vin 20 mg/m²/week; 5FU 800 mg/m²/week+Leukovorin 50 mg/m²/week, FIG. 1F, ifosfamide (IF) 18 mg/m²/week; 5FU 850 mg/m²/week+ Leukovorin 35 mg/m²/week, 5FU 605 mg/m²/week; Vin 20 mg/m²/week+Leukovorin 30 mg/m²/week; FIG. 1G, Vin 20 mg/m²/week, FIG. 1H, Vin 20 mg/m²/week.

DETAILED DESCRIPTION OF THE INVENTION

Figure 2:
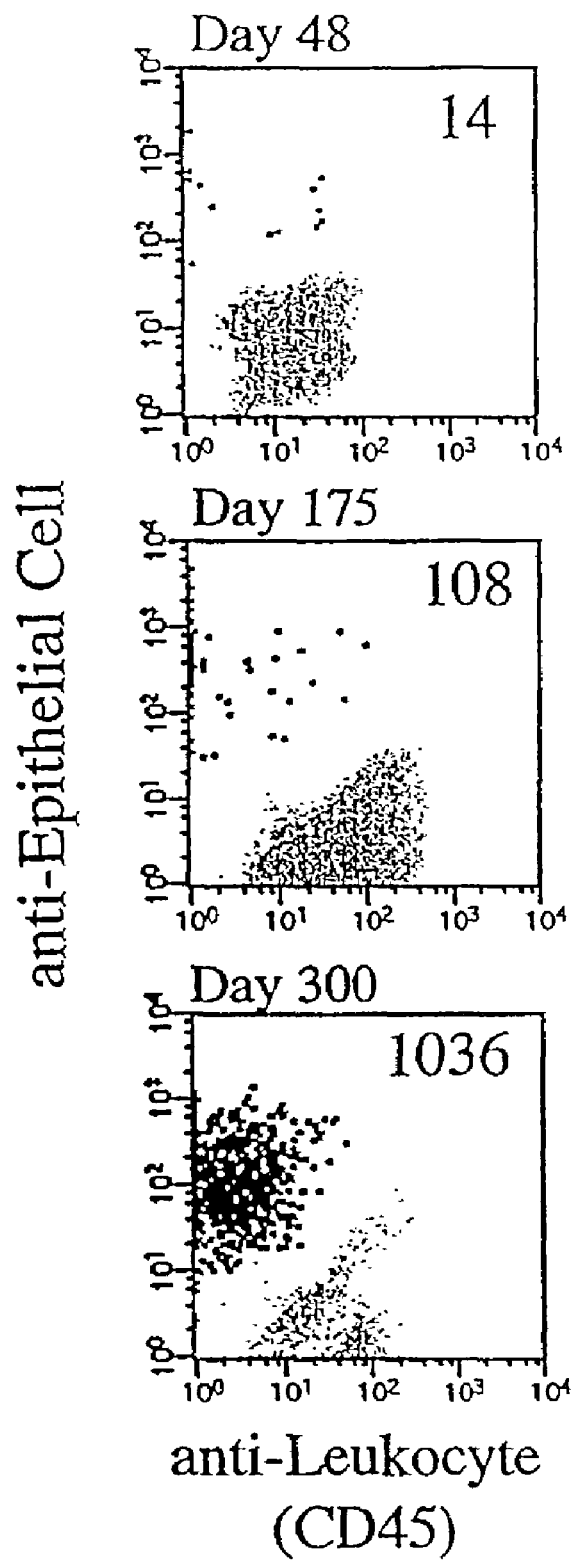
FIG. 2 shows flowcytometric analysis of cell suspensions obtained after immunomagnetic cell selection from 10 ml of blood from a patient having distant metastasis of carcinoma of the breast, drawn 48, 175 and 300 days after this patient entered the study. After immunomagnetic selection, the cells were stained with an epithelial cell specific phycoerythrin (PE) conjugated monoclonal antibody, a leukocyte specific CD45 PerCP conjugated monoclonal antibody and a nucleic acid dye. Events passing a threshold on the nucleic acid dye were acquired into listmode and 85% of the sample was analyzed. The tumor cells are highlighted and illustrated in black and their number is shown in the top right corner; the background events, consisting of residual leukocytes and debris, are illustrated in gray.
Figure 3E:
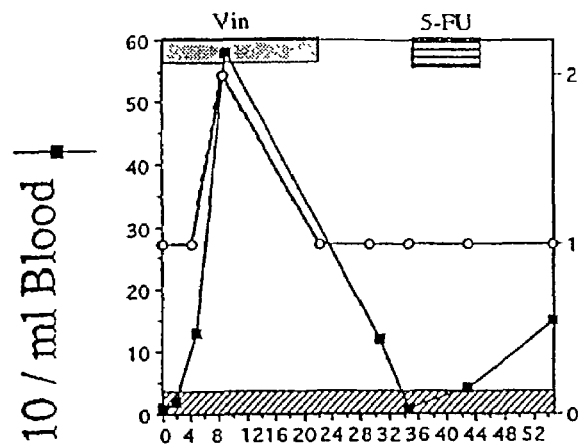
Figure 3F:
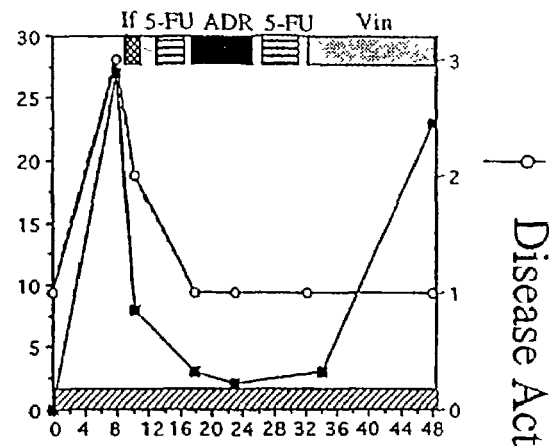
Figure 3G:
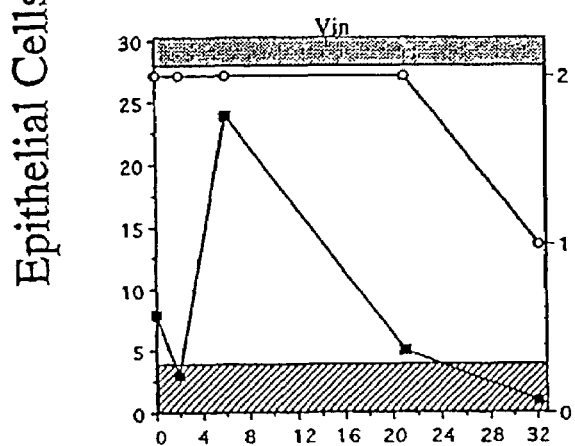
Figure 3H:
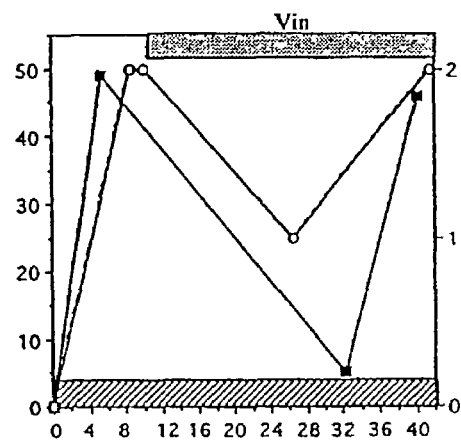

According to a preferred embodiment, the present invention provides compositions, methods and kits for the rapid and efficient isolation of rare target bioentities from biological samples. The methods described may be used effectively to isolate and characterize tumor cells present in a blood sample while at the same time minimizing the selection of non-specifically bound cells.

Many clinicians believe that cancer is an organ-confined disease in its early stages. Based on the data presented herein, it appears that this notion is incorrect. Indeed, the data reveal that cancer is often a systemic disease by the time it is first detected using methods currently available. Hence, the presence of tumor cells in the circulation can be used to screen for cancer in place of, or in conjunction with, other tests, such as mammography, or measurements of PSA. By employing appropriate monoclonal antibodies directed to specific markers on or in cells, or by using other assays for cell protein expression, or by the analysis of cellular mRNA, the organ origin of such cells may readily be determined, e.g., breast, prostate, colon, lung, ovarian or other non-hematopoietic cancers. Thus, in cases where cancer cells can be detected, while there are essentially no clinical signs of a tumor, it will be possible to identify their presence as well as the organ of origin. Because screening can be done with the relatively simple blood test of the present invention described herein, which functions with a high degree of sensitivity, the test can be thought of as a "whole body biopsy". Furthermore, based on the data set forth herein, cancer should be thought of as a blood borne disease characterized by the presence of potentially very harmful metastatic cells, and therefore, treated accordingly. In cases where there is absolutely no detectable evidence of circulating tumor cells, e.g., following surgery, it may be possible to determine from further clinical study whether follow-up treatment, such as radiation or chemotherapy is required. Determining the need not to treat, given the costs of such therapies, is a significant and beneficial piece of clinical information.

It is also clear from the present data that the number of tumor cells in the circulation is related to the stage of progression of the disease, from its inception to the final phases of disease.

The term "target bioentities" as used herein refers to a wide variety of materials of biological or medical interest. Examples include hormones, proteins, peptides, lectins, oligonucleotides, drugs, chemical substances, nucleic acid molecules, (e.g., RNA and/or DNA) and particulate analytes of biological origin, which include bioparticles such as cells, viruses, bacteria and the like. In a preferred embodiment of the invention, rare cells, such as fetal cells in maternal circulation, or circulating cancer cells may be efficiently isolated from non-target cells and/or other bioentities, using the compositions, methods and kits of the present invention. The term "biological specimen" includes, without limitation, cell-containing bodily, fluids, peripheral blood, tissue homogenates, nipple aspirates, and any other source of rare cells that is obtainable from a human subject. An exemplary tissue homogenate may be obtained from the sentinel node in a breast cancer patient. The term "determinant", when used in reference to any of the foregoing target bioentities, may be specifically bound by a biospecific ligand or a biospecific reagent, and refers to that portion of the target bioentity involved in, and responsible for, selective binding to a specific binding substance, the presence of which is required for selective binding to occur. In fundamental terms, determinants are molecular contact regions on target bioentities that are recognized by receptors in specific binding pair reactions. The term "specific binding pair" as used herein includes antigen-antibody, receptor-hormone, receptor-ligand, agonist-antagonist, lectin-carbohydrate, nucleic acid (RNA or DNA) hybridizing sequences, Fc receptor or mouse IgG-protein A, avidin-biotin, streptavidin-biotin and virus-receptor interactions. Various other determinant-specific binding substance combinations are contemplated for use in practicing the methods of this invention, such as will be apparent to those skilled in the art. The term "antibody" as used herein, includes immunoglobulins, monoclonal or polyclonal antibodies, immunoreactive immunoglobulin fragments, and single chain antibodies. Also contemplated for use in the invention are peptides, oligonucleotides or a combination thereof which specifically recognize determinants with specificity similar to traditionally generated antibodies. The term "detectably label" is used to herein to refer to any substance whose detection or measurement, either directly or indirectly, by physical or chemical means, is indicative of the presence of the target bioentity in the test sample. Representative examples of useful detectable labels, include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules. The phrase "to the substantial exclusion of" refers to the specificity of the binding reaction between the biospecific ligand or biospecific reagent and its corresponding target determinant. Biospecific ligands and reagents have specific binding activity for their target determinant yet may also exhibit a low level of non-specific binding to other sample components. The term "early stage cancer" as used herein refers to those cancers which have been, clinically determined to be organ-confined. Also included are tumors too small to be detected by conventional methods such as mammography for breast cancer patients, or X-rays for lung cancer patients. While mammography can detect tumors having approximately $2\times10^8$ cells, the methods of the present invention should enable detection of circulating cancer cells from tumors approximating this size or smaller. The term "enrichment" as used herein refers to the enrichment of mononuclear cells from a biological sample. In cases where peripheral blood is used as the starting materials, red cells are not counted when assessing the extent of enrichment. Using the method of the present invention, circulating epithelial cells may be enriched relative to leucocytes to the extent of at least 2,500 fold, more preferably 5,000 fold and most preferably 10,000 fold. The preferred magnetic particles for use in carrying out this invention are particles that behave as colloids. Such particles are characterized by their sub-micron particle size, which is generally less than about 200 nanometers (nm) (0.20 microns), and their stability to gravitational separation from solution for extended periods of time. In addition to the many other advantages, this size range makes them essentially invisible to analytical techniques commonly applied to cell analysis. Particles within the range of 90-150 nm and having between 70-90% magnetic mass are contemplated for use in the present invention. Suitable magnetic particles are composed of a crystalline core of superparamagnetic material surrounded by molecules which are bonded, e.g., physically absorbed or covalently attached, to the magnetic core and which confer stabilizing colloidal properties. The coating material should preferably be applied in an amount effective to prevent non specific interactions between biological macromolecules found in the sample and the magnetic cores. Such biological macromolecules may include sialic acid residues on the surface of non-target cells, lectins, glyproteins and other membrane components. In addition, the material should contain as much magnetic mass/nanoparticle as possible. The size of the magnetic crystals comprising the core is sufficiently small that they do not contain a complete magnetic domain. The size of the nanoparticles is sufficiently small such that their Brownian energy exceeds their magnetic moment. As a consequence, North Pole, South Pole alignment and subsequent mutual attraction/repulsion of these colloidal magnetic particles does not appear to occur even in moderately strong magnetic fields, contributing to their solution stability. Finally, the magnetic particles should be separable in high magnetic gradient external field separators. That characteristic facilitates sample handling and provides economic advantages over the more complicated internal gradient columns loaded with ferromagnetic beads or steel wool. Magnetic particles having the above-described properties can be prepared by modification of base materials described in U.S. Pat. Nos. 4,795,698, 5,597,531 and 5,698,271. Their preparation from those base materials is described below.

Malignant tumors are characterized by their ability to invade adjacent tissue. In general, tumors with a diameter of 1 mm are vascularized and animal studies show that as much as 4% of the cells present in the tumor can be shed into the circulation in a 24 hour period (Butler, T P & Gullino P M, 1975 Cancer Research 35:512-516). The shedding capacity of a tumor is most likely dependent on the aggressiveness of the tumor. Although tumor cells are shed into the circulation on a continous basis, it is believed that none or only a small fraction will give rise to distant metastasis (Butler & Gullino, supra). Using the following assumptions, one can approximate the frequency of tumor cells in circulation as follows: 1. A tumor with a diameter of 1 mm contains $10^7$ cells, and 4% or $4 \times 10^5$ cells will be shed into the circulation in a 24 hour period; 2. tumor cells only survive one circulatory cycle; 3. a blood volume of about 5 liters; and 4. a cardiac output of 5000 ml/minute. In such a case, the frequency of tumor cells in peripheral blood of a patient with a 1-mm diameter tumor is approximately 6 tumor cells/100 ml of blood. Increase in tumor mass might be expected to be proportional to an increase in the frequency of the circulating tumor cells. If this were found to be the case, methods available with this level of sensitivity would facilitate both assessing tumor load in patients with distant metastasis and also assessing tumor load in patients with localized disease. Detection of tumor cells in peripheral blood of patients with localized disease has the potential not only to detect a tumor at an earlier stage but also to provide indications as to the potential invasiveness of the tumor.

Several studies report the presence of carcinoma cells in leukopheresis products harvested from patients with carcinoma of the breast for autologous peripheral blood stem cell transplantation (Brugger W, et al. (1994) Blood 83:636-640; Brockstein B E, et al. (1996) J of Hematotherapy 5:617; Ross A A, et al. (1993) Blood 82:2605; Ross A A. (1998) J of Hematotherapy. 7:9-18; Moss T J, et al. (1994) J. Hematotherapy. 3:163-163). These findings prompted criticism of the use of this procedure for autologous transplantation since the tumor cells in the transplant product have the potential to establish metastasis (Racila E, et al. (1998) PNAS USA. 95:4589-4594). Additionally, it was found that leukopheresis products were more likely to contain tumor cells when obtained from individuals with disseminated disease (Brugger et al., 1994, supra). These studies, however, do not report quantitative data, nor do they report that tumor cells can be found in peripheral blood of patients with localized disease. Given these observations, one may hypothesize that a highly sensitive and quantitative test that counts the number of tumor cells in peripheral blood may be used to determine actual tumor load. To assess the feasibility of such testing, a sensitive cellular assay was developed which allows precise enumeration of circulating carcinoma cells that is limited only by the blood volume to be tested.

It should be noted that a number of different cell analysis platforms can be used to identify and enumerate the enriched samples. Examples of such analytical platforms are Immunicon's CellSpotter system, a magnetic cell immobilizer for manual observation of cells, and the CellTracks system, an automatic optical scanning magnetic cell immobilizer described in U.S. patent application Ser. No. 08/931,067 and Ser. No. 08/867,009 respectively. Both of the aforementioned U.S. Patent Applications are incorporated by reference herein as disclosing the respective apparatus and methods for manual or automated quantitative and qualitative cell analysis.

Other analysis platforms include Laserscanning Cytometry (Compucyte), bright field base image analysis (Chromavision), and Capillary volumetry (Biometric imaging).

The enumeration of circulating epithelial cells in blood using the methods and compositions of a preferred embodiment of the present invention is achieved by immunomagnetic selection (enrichment) of epithelial cells from blood followed by the analysis of the samples by multiparameter flowcytometry. The immunomagnetic sample preparation is important for reducing sample volume and obtaining a $10^4$ fold enrichment of the target (epithelial) cells. The reagents used for the multiparameter flowcytometric analysis are optimized such that epithelial cells are located in a unique position in the multidimensional space created by the list-mode acquisition of two lightscatter and three fluorescence parameters. These include 1) an antibody against the pan-leucocyte antigen, CD45 to identify leucocytes (non-tumor cells); a cell type specific or nucleic acid dye which allows exclusion of residual red blood cells, platelets and other non-nucleated events; and 3) a biospecific reagent or antibody directed against cytokeratin or an antibody having specificity for an EpCAM epitope which differs from that used to immunomagnetically select the cells.

It will be recognized by those skilled in the art that the method of analysis of the enriched tumor cell population will depend on the intended use of the invention. For example, in screening for cancers or monitoring for recurrence of disease, as described hereinbelow, the numbers of circulating epithelial cells can be very low. Since there is some "normal" level of epithelial cells, (very likely introduced during venipuncture), a method of analysis which identifies epithelial cells as normal or tumor cells is desirable. In that case, microscopy based analyses may prove to be the most accurate. Such examination might also include examination of morphology, identification of known tumor markers and or oncogenes. Alternatively, in disease states wherein the number of circulating epithelial cells far exceeds that observed in the normal population, an analytical method which enumerates such cells should be sufficient. The determination of patient status according to the methods described herein is made based on a statistical average of the number of circulating rare cells present in the normal population. Levels of circulating epithelial cells in the early stage cancer patient and in patients with aggressive metastatic cancer can also be statistically determined as set forth herein.

The following methods are provided to facilitate the practice of the present invention.

Patients. With informed consent, 8-20 ml blood samples were obtained from controls and patients with carcinoma of the breast, prostate and colon. Blood was drawn from some of these patients at several time points over a period of one year. The blood samples were drawn into Vacutainer tubes (Becton-Dickinson) containing EDTA as anticoagulant. The samples were kept at room temperature and processed within 24 hours after collection. The circulating epithelial cells were enumerated in peripheral blood samples from breast, prostate and colon cancer patients and in normal controls with no evidence of malignant disease. Date of diagnosis, therapeutic interventions and clinical status were retrieved from the patient's charts. The institutional review board of the collaborating institutions approved the protocol.

Sample preparation. Monoclonal antibodies specific for epithelial cell adhesion molecule (EpCAM) are broadly reactive with tissue of epithelial cell origin (Stahel R A, et al. Int J Cancer Suppl. 8:6-26 (1994); Momburg F, et al. Cancer research. 47:2883-2891 (1987); Gaffey M J, et al. Am J Surg Path. 16:593-599 (1992)). The GA73.3 or MJ37 EpCAM antibodies recognizing two different epitopes on EpCAM (kindly provided by D Herlyn (Herlyn D, et al. J Immunol Methods. 73:157-167 (1984)) Wistar Institute, Philadelphia, Pa. and M J Mattes (De Leij L, et al. Int J Cancer Suppl. 8:60-63 (1993)) Center for Molecular Medicine and Immunology, NJ) were coupled to magnetic nanoparticles (ferrofluids) (Liberti P A & Piccoli S P, U.S. Pat. No. 5,512,332 (1996), Immunicon, Huntingdon Valley, Pa.). Blood was incubated with the anti-EpCAM conjugated ferrofluid for 15 minutes in disposable tubes with an internal diameter of 13 mm. The tubes were placed into a separator composed of four opposing magnets for 10 minutes (QMS13, Immunicon, Huntingdon Valley, Pa.). After separation, the blood was aspirated and discarded. The tube was taken out of the magnetic separator and the collected fraction was resuspended from the walls of the vessel with 2 ml of FACS permeabilization solution (BDIS, San Jose, Calif.) and placed in the magnetic separator for 5 minutes. The solution was aspirated and discarded and the cells were resuspended in 150 µl of cell buffer (PBS, 1% BSA, 50 mM EDTA, 0.1% sodium azide) to which phycoerythrin (PE) conjugated anti-cytokeratin (CAM5.2 Monoclonal antibody) and Peridinin Chlorophyll Protein (PerCP)-labeled CD45 were added at saturating conditions. After incubation for 15 minutes, 2 ml of cell buffer was added and the cell suspension was magnetically separated for 5 minutes. After discarding the nonseparated suspension, the collected cells were resuspended in 0.5 ml of the buffer to which the nucleic acid dye used in the Procount system from BDIS, San Jose, Calif., was added according to manufacturer's instructions. In some cases in which the EpCAM antibody MJ37 was used on the ferrofluid, GA73.3 PE was used to identify the selected epithelial cells. In these cases no permeabilization of the cells is required. Reagents for flowcytometry were kindly provided by BDIS, San Jose, Calif.

An exemplary method for determining the tissue source of circulating epithelial cells employs cytochemical and immunological identification techniques. Primary monoclonal antibodies recognizing cytokeratins 5, 6, 8, 18 (CK, 5D3, LP34, Novocastra), MUC-1 glycoprotein (MUC-1, Ma695 Novocastra) or prostate specific antigen (PSMA), clone J591 obtained from Dr. Neil Bander (University of Texas Medical Center, Dallas, Tex.) was added to the slides after blocking non-specific binding sites with 5% BSA for 30 minutes. The samples were incubated for 20 minutes at room temperature, washed twice in PBS for 5 minutes and then exposed to secondary rabbit anti-mouse Ig (Z0259, Dako Corp., Carpenteria, Calif.) for another 20 minutes. After two more washes, the samples were incubated with alkaline-phosphatase-anit-alkaline phosphatase (APAAP) rabbit Ig complexes for 15 minutes. Finally, the enzyme-substrate (New Fuchsin, Dako Corp. CA) was added resulting in the development of red precipitates. The nucleus was counterstained with hemotoxylin. The data were recorded using a Kodak digital camera attached to a light microscope. Data could be stored on CD for later reference.

Sample analysis. 85% of the samples were analyzed on a FACSCalibur flowcytometer (BDIS, San Jose, Calif.). The data were acquired in listmode using a threshold on the fluorescence of the nucleic acid dye. Multiparameter data analysis was performed using Paint-A-Gate$^{Pro}$ (BDIS, San Jose, Calif.). Analysis criteria included size defined by forward light scatter, granularity defined by orthogonal light scatter, positive staining with the PE labeled cytokeratin monoclonal antibody and no staining with the PerCP labeled CD45 monoclonal antibody. For each sample, the number of events present in the region typical for epithelial cells was normalized to 10 ml of blood.

The following examples are provided to facilitate the practice of the present invention. These examples are not intended to limit the scope of the invention in any way.

EXAMPLE 1

Formulation of Improved Magnetic Nanoparticles for the Efficient Isolation of Rare Cells from Whole Blood Rare cells (e.g., tumor cells in patients with epithelial derived tumors, fetal cells in maternal blood or the like) can be present in frequencies below one rare cell per ml of blood. The number of blood smears required to detect such rare cells is prohibitively large. Assuming 10 rare cells in 10 ml of blood, which corresponds to 10 tumor cells in 5-10×10$^7$ white blood cells (leukocytes), cells can be transferred to a microscope slide by cytocentrifugation or by settling, stained with an antibody specific for the rare cells of interest and read manually or automatically. The maximum number of cells that can be transferred to one slide is about 500,000 cells which means 100-200 slides are required to process 10 ml of blood. The time required for analysis by this approach makes it impractical and economically unfeasible. Consequently, enrichment methods such as sample volume reduction and removal of erythrocytes and platelets by density gradient separation or erythrocyte lysis procedures are used for isolating rare cells so as to significantly reduce the number of slides to be analyzed.

As noted above, magnetic enrichment is the preferred method for cell separations and, ideally, the nanoparticles employed for this purpose should not have to be removed prior to analysis. Accordingly, the nanoparticles should be small enough so as not to interfere with analytical measurements, i.e. below about 250 nm. Most preferably, the nanoparticles are below 220 nm so as to make them filter sterilizable. Furthermore, the nanoparticle should be large enough and magnetically responsive enough to permit cell separation from simple laboratory tubes, i.e., test tubes, centrifuge tubes, vacutainers and the like in external gradient magnetic separators. Again, as previously noted internal gradient devices are cumbersome, costly and inefficient for the recovery of rare cells. Also, the nanoparticles and magnetic device should give high and reproducible recovery with low non-specific binding. U.S. Pat. No. 5,597,531 describes the synthesis of highly magnetic particles, referred to as direct coated (DC) particles which have many of these characteristics. These nanoparticles are composed of quasispherical agglomerates of crystalline magnetite or other magnetic oxides which are coated with polymers or proteins (based coated magnetic particles). Because of their structure (magnetic core and polymer coat where the core diameter is >>> than the thickness of the coat) they are about 80-85% magnetic mass. The non-specific bindings of these nanoparticles are in the range of 5-8% and they are, therefore, not very practical for rare cell separations. Thus if one is enriching cells present at one cell per ml then at 80% capture efficiency, the best result to be expected using 10 mls of whole blood (considering leukocytes alone) would be 8 cells recovered in a total of 4 million, i.e. a 16-17 fold enrichment. The magnetic particles described in U.S. Pat. No. 5,597,531 do, however, have the appropriate magnetic properties to perform separations with open field separators and from simple laboratory tubes. Further, their mean size is well under the limit suggested above and, hence, they do not interfere with various analytical procedures. Based on extensive studies with those materials, the major contributing factor to non-specific binding to cells was discovered to be the presence of bare crystalline iron oxides on the nanoparticles due to incomplete coating. Such incompletely coated crystals have a sufficiently high positive charge at physiological pH that they are very likely to bind strongly to biological macromolecules, such as negatively charged sialic acid on cell surfaces. An improved method for making particles is described in U.S. Pat. No. 5,698,271. These materials are an improvement over those disclosed in the '531 patent in that the process includes a high temperature coating step which markedly increases the level of coating. Nanoparticles made with bovine serum albumin (BSA)

coating using this process, for example, have a 3-5-fold lower non-specific binding characteristic for cells when compared to the DC-BSA materials of U.S. Pat. No. 5,579,531. This decrease in non-specific binding has been shown to be directly due to the increased level of BSA coating material. When such nanoparticles were treated so as to remove BSA coating, non-specific binding returns to high levels. It was thus determined that a direct relationship exists between the amount of BSA coated on iron oxide crystal surfaces and the nonspecific binding of cells. Typically, the non-specific binding of cells from whole blood with these particles was 0.3% which is significantly better than those produced from U.S. Pat. No. 5,579,531. Thus, from 10 mls of whole blood there would be about 200,000 non-target cells that would also be isolated with the cells targeted for enrichment.

In addition to the non-specific binding problem, to be addressed further below, it was found that when different lots of magnetic particles, manufactured as described in U.S. Pat. Nos. 5,579,531 and 5,698,271 were used in rare cell depletions or enrichments, recoveries were inconsistent. Sometimes recoveries were 85-95% and other times they could be 40-50% using the same model system. As the process for manufacturing these materials results in a size dispersion of considerable range (30 nm to 220 nm), it was suspected and confirmed that the size distribution and particularly the presence of small nanoparticles markedly affected target recovery. Since small nanoparticles (30 to 70 nm) will diffuse more readily they will preferentially label cells compared with their larger counterparts. When very high gradients are used, such as in internal gradient columns, the performance of these materials regardless of size make little difference. On the other hand, when using external gradients, or gradients of lesser magnitude than can be generated on microbead or steel wool columns, the occupancy of small nanoparticles on cells has a significant effect. This was conclusively shown to be the case by fractionating DC nanoparticles and studying the effects on recovery. Based on these studies and other optimization experiments, means for fractionating nanoparticles magnetically or on columns was established where base coated magnetic particles could be prepared that were devoid of excessively small or large nanoparticles. For example, base coated particles of mean diameter 100 nm can be produced which contain at best trace amounts of material under 80 nm or over 130 nm. Similarly material of about 120 nm can be made with no appreciable material under 90-95 nm and over 160 nm. Such materials performed optimally with regard to recovery and could be made sub-optimal by the inclusion of 60-70 nm nanoparticles. The preferred particle size range for use in practicing this invention is 90-150 nm for base coated magnetic particles, e.g., BSA-coated magnetite. Particles falling within this preferred range may be obtained using the procedure described by Liberti et al. In Fine Particles Science and Technology, 777-90, E. Pelizzetti (ed.) (1996).

To further address the non-specific binding problem, several routes for making antibody conjugated direct nanoparticles were attempted. Monoclonal antibody specific for rare cells can be directly coupled to, for example, the BSA base coating on the DC magnetic particles by standard heterobifunctional chemistry (referred to herein as direct coupling method). Heterobiofunctional linkers used for these purposes include sulfo-MCCC and sulfosuccinimidil-4-[maleimidomethyl]cyclohexane-1-carboxylate. In another approach, biotinylated monoclonal antibodies can be coupled to streptavidin which has been coupled to the base coated particles. This conjugate method is referred to herein as a piggyback method. In this process, streptavidin is coupled to the base coated magnetic particles by the same chemistry as the direct coupling method. In one piggyback coupling method, monobiotinylated antibody is allowed to react with streptavidin magnetic particles for 1 hour and then the remaining streptavidin binding sites quenched with free biotin. It is important to quench the remaining streptavidin sites after antibody coupling to prevent binding of any biotinylated antibody to magnetic particles during isolation of rare cells or the cell analysis step. Furthermore, it has been shown that this means for quenching streptavidin is effective for counteracting non-specific binding. Incubation of such materials under a variety of conditions with biotinylated fluorescent macromolecules results in no bound fluorescence. For comparison, anti-EpCAM antibody (GA73.3 obtained from the Wistar Institute, Philadelphia, Pa.) was coupled to magnetic particles by both methods. Both magnetic particles were then compared for the selection of cells from the colon tumor cell line (Colo-205) spiked into whole blood as well as for the non-specific binding (NSB) or carry-over of leukocytes. The leukocytes present in the final sample were a combination of leukocytes non-specifically bound to magnetic particles and carry-over of cells from the wash steps. Note that following magnetic separation, it is necessary to wash away any cells which were in contact with the tube at the start of the separation or that were transported non-magnetically during the separation process. The following table shows the comparison of those two magnetic particles.

| Magnetic particles | Recovery of spiked Colo-205 cells (%) | NSB and carry over leukocytes (%) |
| --- | --- | --- |
| EpCAM antibody directly coupled to magnetic particles (lot.# 120325-1) | 78-82 | 0.1-0.3 |
| EpCAM antibody coupled to magnetic particles by piggyback method (lot.# 120607-2) | 67-78 | 0.05-0.1 |

The first thing noted is that merely coupling antibody or Streptavidin to BSA base particles significantly reduces non-specific binding (data not shown). This is believed to be due to decreasing the accessability of "bare" crystal surfaces to cells for binding. The above table demonstrates that the recovery of spiked cells is comparable for both types of magnetic particles. However, the non-specific binding of leukocytes was 3-fold higher when using the direct antibody coupled magnetic particles. This difference, albeit relatively small, becomes significant when a large volume of blood is processed and analyzed. A reasonable explanation based on many supporting observations for the difference between the two types of magnetic particles is that there are more layers of protein on magnetic particles synthesized using the piggyback coupling method. The surface of the magnetic crystals are thus coated more extensively with multiple layers of protein and appear to be sterically "protected". This prevents binding of non-target cells to the magnetic particles.

In the piggyback coupling method, a limited number of streptavidin binding sites on the magnetic particles are occupied with biotin-antibody and the remainder are saturated with free biotin by the quench process described above. In yet another coupling method, the excess streptavidin binding sites were quenched and saturated with mono-biotin-BSA instead of free biotin. The rationale for this approach is that quenching with monobiotin BSA should further sterically inhibit cells from coming in contact with uncoated regions of the nanoparticles, i.e. give better coverage of the nanoparticles. It was shown by carbon analysis that this process increases the amount of protein coupled to the particles. The two magnetic particle preparations were compared in experiments assessing recovery of spiked Colo 205 from whole blood and for non-specific binding of leukocytes. The results are presented in the following table.

| Magnetic particles | Recovery of Colo 205 cells (%) | NSB and carry over leukocytes (%) |
| --- | --- | --- |
| EpCAM antibody coupled magnetic particles - quenched excess streptavidin sites with free biotin (lot. # 131022-1) | 93<br>87<br>85 | 0.08<br>0.1<br>0.1 |
| EpCAM antibody coupled magnetic particles - quenched excess streptavidin sites with biotin-BSA (lot. # 131022-2) | 87<br>83<br>85 | 0.01<br>0.03<br>0.02 |

Monobiotin-BSA may be prepared by conjugating a limited amount of biotin to BSA, such that 30-40% of the resultant product has no bound biotin.

In summary, magnetic particles having a homogeneous size distribution and biotin-BSA quenched streptavidin binding sites performed extremely well in the assay methods of the present invention. A good recovery of the spiked epithelial tumor cells and almost an order of magnitude reduction in nonspecific binding is obtained using these particles, compared with the biotin blocked nanoparticles. Thus, these materials and the results obtained with them define a very useful product which can be further optimized. The improved ferrofluid product is made as magnetic as possible, is coated so as to exclude all possible interactions of the magnetic core with any substances in blood including cells (presumably coated with a nonporous monolayer) and are well defined in its size range and distribution. In the preferred situation, a coat material is used which does not interact with biological materials. Where such interactions are unavoidable, a means for blocking them is required. For a material to be as magnetic as possible, those produced as described in U.S. Pat. Nos. 5,579,531 and 5,698,271 are preferred starting materials. They are preferable because they are composed of large magnetic cores with an apparent but not complete monolayer of base coating material. For a 100 nm nanoparticle coated with BSA, the core will be about 90 nm of an appropriate magnetic oxide such as magnetite. Such nanoparticles because of the relative size of the cores and coat material are clearly as magnetic as is possible. This is apparent if one considers that the function of the coating is to keep the nanoparticles from undesired interactions with each other which would lead to macroscopic agglomeration. The coating also promotes sufficient interactions with solvent molecules so as to maintain colloidal behavior and provides a convenient chemical means for coupling. The nanoparticles of U.S. Pat. Nos. 5,579,531 and 5,698,271 are also preferred as a starting material as they have sufficient monolayer coating wherein "holes" in the monolayer can be filled in several ways, viz., sterically and physically. Clearly any coating that promotes the effective complete coverage of the magnetic core, so as to inhibit interactions of the core material with blood components or any other non-specific effects in any other system would be suitable. The less mass such a coating might add to the nanoparticles the better, so as to maximize the magnetic mass to nanoparticle mass ratio.

EXAMPLE 2

Enumeration of Circulating Epithelial Cells in Patients Treated for Metastatic Breast Cancer FIG. 1 shows the results obtained when tumor cells spiked into whole blood are isolated using the assay methods of the present invention. Panel A shows analysis by microscopy and panel B shows analysis results obtained using flow cytometry. FIG. 2 shows three examples of the flowcytometric analysis of 10 ml blood samples obtained from one patient with metastatic breast carcinoma at three time points, and includes the correlative display of the anti-leukocyte versus anti-epithelial cell antibodies of the flowcytometric analysis. In FIG. 2, Panel A, 14 events are detected and are present in the location typical for epithelial cells. In Panel B, 108 epithelial cells are detected and in Panel C 1036 epithelial cells are detected.

The number of events passing the threshold set on the nucleic acid dye in the analysis of the 10-ml blood sample varied between 5,000 and 50,000 events. These events consist of cellular debris and leukocytes. In analyzing the blood of 32 controls, the number of events present in the region typical for epithelial cells ranged from 0-4/10 ml of blood (mean=1.0, SD=1.2).

Eight breast cancer patients had active metastatic disease during the period of study. In these patients, the number of epithelial cells in 10 ml of blood varied within the range of 0 to 1036. The activity of the disease was assessed by subjective criteria, i.e. bone pain, dyspnea etc. and objective criteria, X-rays, bone scans, CT scan, MRI and lymph node size. Patients were classified in categories 0 through 4, as set out in Table 1.

TABLE I

Classification of patients according to clinical activity of the disease after surgical intervention

| Category | Criteria |
| --- | --- |
| 0 | No evidence of disease at any time point after surgical intervention |
| 1 | Evidence of disease at one time point after surgical intervention |
| 2 | Evidence of disease under control |
| 3 | Active progressive disease |
| 4 | Life threatening disease |

The dynamics of epithelial cell counts in the blood of 8 patients with metastatic disease are presented in FIG. 3. The shaded area in the plots indicates the range at which positive events were detected in the controls. The plots also indicate when chemotherapy was administered. FIG. 3, panel A shows a patient with life threatening disease and 200 epithelial cells/10 ml of blood at the time she entered the study. High dose adriamycine reduced the number within the normal range, but it rose again after adriamycine was discontinued. After a second course of adriamycine, the number of epithelial cells dropped significantly, but was still above the normal range. FIG. 3, Panel B shows the course of one patient over a period of 43 weeks. The patient was asymptomatic at the start of the study but was known to have bone metastasis in the past. Epithelial cells were detected above normal levels and steadily increased during the period studied. A brief decline in the number of epithelial cells was found after a course of high dose adriamycine was administered. The activity of disease in this patient clearly increased during this period. In FIG. 3, Panels C and D, two patients are shown with less disease activity. In these patients, the changes in the number of epithelial cells over time also reflected the changes in the activity of the disease. In the patients shown in Panels E and F, the number of peripheral blood epithelial cells increased at the last time point studied while the patients still were without symptoms.

In the case shown in Panel G, no epithelial cells were detected at the first time point studied which was three years after breast cancer surgery (T2N1M0). Four weeks later, 50 epithelial cells in 10 ml of blood were detected by flowcytometry. The patient at this time had no clinical signs of disease recurrence. An additional blood sample was analyzed to obtain morphological confirmation that the cells detected by flowcytometry had features consistent with those of malignant cells.

FIG. 4A shows two cells with a large nuclear to cytoplasmic ratio and which positively stain with Cytokeratin, both features being consistent with tumor cells of epithelial cell origin. Four weeks after this finding, the patient had an axillary lymph node biopsy. Cells obtained from the biopsy proved to be of malignant origin. Although an X-ray at this time did not show signs of pulmonary metastasis, a CT scan performed two weeks later showed evidence of pulmonary metastasis. The patient had no symptoms from the pulmonary metastasis. The patient reacted well to Vinorelbine as measured by the disappearance of the axillary lymphnode involvement. The peripheral blood epithelial cell number dropped to levels just above the normal range. Twenty-eight weeks after initiation of the treatment, the peripheral blood epithelial cell number increased and by physical examination, the axillary node increased in size. The number of peripheral blood epithelial cells in these 8 patients with metastatic disease of carcinoma of the breast clearly reflected the activity of the disease and the response to treatment or the lack thereof during the time period studied.

The experiments described above were performed using colloidal magnetic nanoparticles. In this example, the efficiency of larger size magnetic beads for the selection of tumor cells present at a low frequency in blood was also evaluated to determine whether micron size beads can also be used to select tumor cells even though as described above, nanometer size magnetic particles are considered preferable for this application.

As mentioned previously, disadvantages are encountered with the use of larger size beads. These are: (i) the beads are too large to diffuse thus collisions of the beads with target cells present at a low frequency requires mixing (ii) the beads settle very fast, furthering the need for continuous mixing and (iii) large size beads cluster around cells and obscure analysis. Accordingly the large size beads need to be removed from the cell surface prior to visualization or analysis. In accordance with the present invention, it has been found that the efficiency of cell selection with larger beads can be improved by increasing the concentration of beads and increasing the incubation time with continuous mixing to facilitate binding to rare target cells. In this example, 2.8 µm Dynal anti-epithelial cell beads (Dynal, NY) were used to test the efficiency of tumor cell selection from blood in a model study under optimum conditions for large beads. These beads are conjugated with a monoclonal antibody specific for epithelial tumor cells. A known number of tumor cells (cancer cell line) were spiked into normal blood to determine the recovery after selection with beads. The tumor cells were prelabeled with a fluorescent dye to differentiate them from blood cells during detection. The protocol was followed as recommended by the manufacturer.

Whole blood (5 ml) was added to a 15 ml polystyrene centrifuge tube followed by the addition of 20±3 fluorescently labeled SKBR-3 (breast cancer cell line) cells. SKBR-3 cells were prestained with a nucleic acid staining dye (Hoescht) to allow detection after the selection by beads. The blood was diluted with 5 ml of Dulbecco's PBS containing 5 mM EDTA and mixed with the diluted blood for 15 minutes at 4° C. on a rocker. 100 µl of Dynal anti-epithelial cell beads containing $50 \times 10^6$ beads were added to the blood sample and incubated for 30 minutes at 4° C. with mixing on a rocker. Note that the number of beads used were similar to total white blood cells i.e. one bead per white cell. The magnetically labeled cells were separated by placing the sample tube into Dynal MPC magnetic separator for 6 minutes.

After aspirating the supernatant, the collected cells were resuspended in 3 ml of Dulbecco's PBS containing 0.1% BSA. The sample tube was placed back into Dynal's MPC for 6 minutes to remove any carry-over blood cells. The magnetically bound cells were resuspended in 200 µl of Dulbecco's PBS containing 0.1% BSA after aspiration of the supernatant.

The final sample, containing selected tumor cells, non-specifically bound blood cells and excess free magnetic beads, was spotted onto an immunofluorescent slide to detect tumor cells. The 200 µl sample was spotted into 10 different wells to disperse free magnetic beads. The fluorescently stained tumor cells present in each well were counted using a fluorescent microscope. The results are shown in the Table II:

TABLE II

| Experiment No. | Tumor cells recovered | % Recovery |
| --- | --- | --- |
| 1 | 16 | 80 |
| 2 | 17 | 85 |
| 3 | 10 | 50 |
| 4 | 11 | 54 |

The results show that, on average, 67% of the spiked tumor cells were recovered from blood by Dynal magnetic beads. This suggests that tumor cells present in blood can be selected efficiently with larger size magnetic beads under optimum conditions. In this example, however, only the selection of tumor cells from blood was evaluated without performing any analysis. Further the efficiency of recovery could be determined because cells were prelabeled with a strong fluorescent dye. The final sample (200 µl) contained $50 \times 10^6$ beads in addition to selected tumor cells (10-17) and non-specifically bound leukocytes. The size of the beads (2.8 um) is similar to that of certain blood cells and occupied most of the surface area on the slide. Therefore, to obtain recovery data, the sample had to be spotted onto several wells in order to sufficiently disperse free magnetic beads so as to allow for detection of recovered tumor cells.

There were also many beads on cell surfaces which precludes viewing and staining of selected tumor cells for further analysis. In this example, tumor cells were prestained with a fluorescent nucleic acid dye and further staining was not necessary for detection. However it is often desirable to identify the tissue of origin of the magnetic bead-bound cells. Such identification is performed using labeled antibodies to detect and characterize tumor cells present in clinical samples. Accordingly, beads have to be removed from cell surfaces and separated from the sample following target cell selection, i.e. before analysis. This is not the case with nanosize magnetic particles because their size does not interfere with cell analysis.

In summary, this example shows that large magnetic beads may also be utilized in the methods disclosed herein for the efficient isolation of circulating tumor cells.

There are several methods available to release beads from cell surfaces which do not significantly damage isolated cells. One method is to displace antibody from the cell surface by adding an excess specific competing reagent in excess which has higher affinity for the involved antigen or antibody. This type of mechanism is used to release beads from CD34 selected cells in clinical applications using a peptide (Baxter Isolex 300). The peptide competes with CD34 antigen for binding to antibody on beads and releases the antibody-bead complex from cells. Another method employs a reversible chemical linker between beads and antibodies.

The chemical linker can be inserted during the conjugation of antibodies to magnetic beads. The chemical link can be cleaved under appropriate conditions to release beads from antibodies. One of the methods currently in use employs a nucleic acid linker to link antibodies to magnetic beads. The nucleic acid linker is a polynucleotide and can be hydrolyzed specifically using DNAse enzyme. Following hydrolysis of the nucleotide bonds present in the nucleic acid linker, the beads are released from the antibodies which remain bound to cells. The released beads can be removed from cell suspension by magnetic separation. The cells which are freed from beads can be used for further analysis by microscopy or flow cytometry.

This example demonstrates that larger size magnetic beads can also be used to isolate tumor cells from blood, provided they are used in high enough concentration to label cells and are then released from cells before analysis.

EXAMPLE 3

Enumeration of Circulating Epithelial Cells in Patients with No Evidence of Disease After Surgery for Carcinoma of the Breast with Curative Intent Peripheral blood of 37 patients between 1 and 20 years after surgery was examined for the presence of epithelial cells by flowcytometry. Up to 7 peripheral blood samples were taken over a one-year period from these patients. In Table III, each of the patients is listed and sorted according to the TNM (tumor, node, and metastasis) stage at the time of surgery followed by the years after surgery. Table III also shows whether or not the patient received treatment (either chemotherapy or hormonal therapy) during the period studied. In 3 of 6 patients with evidence of distant metastasis in the past, but in complete remission at the time of study, epithelial cells were found in the blood at a higher frequency than that found in the control group. Circulating epithelial cells were also found in 9 of 31 patients with no evidence of distant metastasis.

Figure 4:
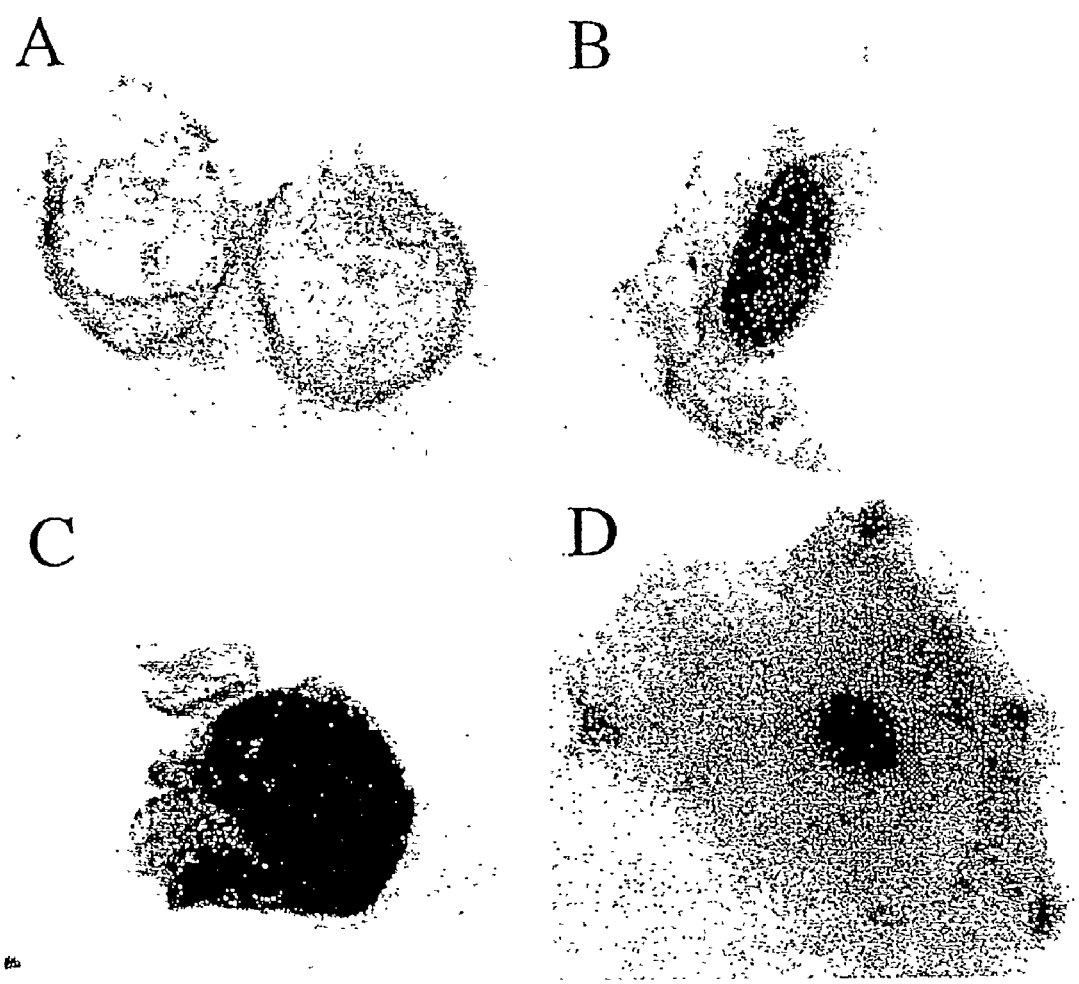
FIGS. 4(A-D) are a series of micrographs showing the results obtained following analysis of immunomagnetically selected cells from peripheral blood of patients with a history of breast carcinoma. A, cells from a patient three years after surgery (T2N1M0) staining positive for cytokeratin, B, cell from a patient eight years after surgery (T2N1M1) in complete remission stained with Wright Giemsa. C and D, cells from a patient 2 years after surgery (T2N0M0) stained with Wright Giemsa. The images were taken with a Pixera digital camera with a 100× objective.

The low number of events present in the region typical for epithelial cells by flowcytometry in these 9 patients does not warrant identifying these events as tumor cells. Cytology obtained by placing the immunomagnetically selected cells on a slide greatly aids in the assessment of their identity as is illustrated in FIG. 4. FIG. 4, panel A, shows two cells staining positive for cytokeratin and obtained from a patient with no evidence of metastatic disease at the time the blood was drawn. Panel B shows a cell from a patient with metastatic disease in the past but in complete remission. In Panels C and D, two cells are shown isolated from the blood of patient 25 at time point 6. The cell shown in Panel C has features consistent with malignancy whereas the cell in Panel D has the appearance of a normal squamous epithelial cell.

TABLE III

Number of epithelial cells identified by flowcytometry in 10 ml of peripheral blood of patients with no evidence of disease after surgery for carcinoma of the breast with curative intent and 32 controls.

| Patient Number | TNM | Ys | Tx | 1 | 2 | 3 | 4 | 5 | 6 | 7 |
|---|---|---|---|---|---|---|---|---|---|---|
| 1 | $T_3N_1M_1$ | 9 | — | 2 | 29 | | | | | |
| 2 | $T_3N_1M_1$ | 16 | H | 0 | | | | | | |
| 3 | $T_2N_1M_1$ | 7 | CT | 10 | 7 | 5 | 6 | 4 | 8 | 7 |
| 4 | $T_2N_1M_1$ | 10 | CT | 1 | 0 | 0 | 1 | 2 | | |
| 5 | $T_2N_1M_1$ | 10 | H | 6 | | | | | | |
| 6 | $T_2N_1M_1$ | 20 | H | 12 | 2 | | | | | |
| 7 | $T_3N_1M_0$ | 1 | H | 0 | | | | | | |
| 8 | $T_3N_1M_0$ | 2 | CT | 0 | 0 | 0 | | | | |
| 9 | $T_3N_1M_0$ | 2 | CT | 0 | 0 | 1 | 0 | | | |
| 10 | $T_3N_1M_0$ | 3 | H | 3 | | | | | | |
| 11 | $T_3N_1M_0$ | 3 | H | 5 | 4 | 0 | 6 | | | |
| 12 | $T_3N_1M_0$ | 3 | H | 3 | 0 | | | | | |
| 13 | $T_3N_1M_0$ | 6 | CT | 6 | 0 | | | | | |
| 14 | $T_3N_1M_0$ | 6 | H | 1 | 1 | | | | | |
| 15 | $T_3N_1M_0$ | 7 | H | 1 | 3 | 3 | | | | |
| 16 | $T_3N_1M_0$ | 3 | H | 0 | | | | | | |
| 17 | $T_2N_1M_0$ | 17 | H | 4 | | | | | | |
| 18 | $T_3N_0M_0$ | 3 | — | 5 | | | | | | |
| 19 | $T_3N_0M_0$ | 5 | H | 1 | | | | | | |
| 20 | $T_3N_0M_0$ | 8 | H | 0 | 6 | 8 | | | | |
| 21 | $T_2M_0M_0$ | <1 | — | 0 | | | | | | |
| 22 | $T_2N_0M_0$ | <1 | H | 0 | | | | | | |
| 23 | $T_2N_0M_0$ | 1 | H | 0 | | | | | | |
| 24 | $T_2N_0M_0$ | 1 | — | 4 | | | | | | |
| 25 | $T_2N_0M_0$ | 2 | CT | 3 | 5 | 1 | 3 | 6 | 2 | |
| 26 | $T_2N_0M_0$ | 3 | CT | 2 | 6 | 3 | 1 | 1 | 0 | 5 |
| 27 | $T_2N_0M_0$ | 6 | H | 18 | | | | | | |
| 28 | $T_2N_0M_0$ | 6 | H | 2 | 1 | | | | | |
| 29 | $T_2N_0M_0$ | 7 | H | 8 | 4 | 2 | | | | |
| 30 | $T_2N_0M_0$ | 8 | H | 0 | 1 | | | | | |
| 31 | $T_2N_0M_0$ | 8 | H | 0 | 6 | 8 | | | | |
| 32 | $T_2N_0M_0$ | 11 | H | 2 | | | | | | |
| 33 | $T_2N_0M_0$ | 20 | H | 4 | | | | | | |
| 34 | $T_1N_0M_0$ | <1 | H | 0 | | | | | | |
| 35 | $T_1N_0M_0$ | 2 | H | 0 | | | | | | |
| 36 | $T_1N_0M_0$ | 17 | — | 0 | | | | | | |
| 37 | $T_2N_0M_0$ | 13 | H | 0 | | | | | | |

N3 controls 2   min 0
    max 4
    mean 1.0 M ± 2SD 3.5

TNM = Tumor, Node, Metastasis
Ys = years after primary surgery
Tx = therapy,
CT = chemotherapy,
H = hormonal therapy,
— = no therapy
1,2,3,4,5,6,7 = subsequent time point at which the number of epithelial cells was determined in years

EXAMPLE 4

Enumeration of Circulating Epithelial Cells in Patients Diagnosed with Breast Cancer before Surgical Intervention.

Table IV summarizes the results obtained following similar clinical trials in which 13 controls and 30 patients with breast cancer were assessed using the assay of the invention. In control individuals the number of epithelial cells in 20 ml of blood ranged from 0-5 (mean 1.5±1.8). In contrast, there was an average of 15.9±17.4 epithelial cells in the 20 ml blood samples of 14 patients with organ-confined carcinoma of the breast (patients classified as $T_xN_oM_o$), 47.4±52.3 in those with nodal involvement, and 122±140 in those with distant metastases. The difference between the control group and patients with carcinoma of the breast, with or without metastasis, was highly significant [P, 0.001 by multiparameter analysis (Kruskal-Wallis)]. The difference between the organ-confined and the distant metastatic group was 0.009(t test). The number of epithelial cells in patients with organ-confined breast cancer was above the cut-off point (mean value plus 3 SD in the control group=6.9) in 12 of 14 cases. Moreover, no individual in the control group had more than 5 events classified as epithelial cells, and only 2 of the 14 patients with organ-confined breast cancer had <7 such events.

TABLE IV

Summary of clinical data

| Number | Healthy Control | No detectable spread | Spread to lymphnodes only | Distant metastasis |
|---|---|---|---|---|
| 1 | 0 | 0 | 7 | 20 |
| 2 | 0 | 4 | 8 | 20 |
| 3 | 0 | 7 | 14 | 20 |
| 4 | 0 | 8 | 93 | 23 |
| 5 | 0 | 8 | 115 | 54 |
| 6 | 0 | 8 | | 62 |
| 7 | 0 | 12 | | 99 |
| 8 | 2 | 13 | | 135 |
| 9 | 2 | 14 | | 152 |
| 10 | 4 | 16 | | 304 |
| 11 | 4 | 18 | | 456 |
| 12 | 5 | 19 | | |
| 13 | | 24 | | |
| 14 | | 72 | | |
| n | 12 | 14 | 5 | 11 |
| mean | 1.5 | 15.9 | 47.7 | 122.5 |

Flowcytometry was used to analyze the positive events obtained from 20 ml of blood from control individuals and from women with breast carcinoma. The numbers of epithelial cells in the blood of controls are statistically different by t test (P≦0.01) and by Kruskall-Wallis nonparametric analysis (P<0.001) from each of the three groups of the breast cancer patients. The data in this table were used to establish a preliminary cut-off value for positive samples. This value was determined by averaging the number of circulating epithelial cells in the normal controls (n=13) and then adding three times the SD. The average was 1.5 and the SD is 1.8. Cut-off: 1.5+5.4=6.9. There is no statistical difference between male and female controls.

EXAMPLE 5

Figure 5C:
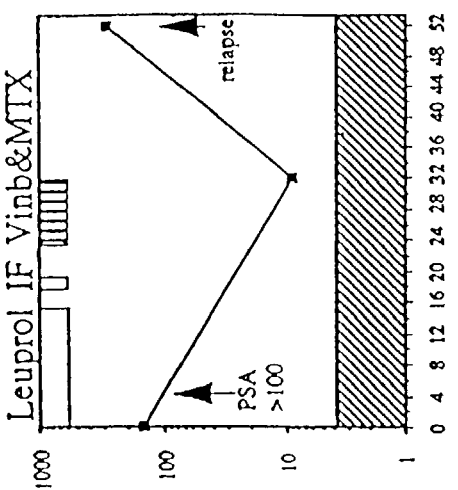
FIGS. 5A-5C are a series of graphs showing the correlation between severity of disease and circulating epithelial cell number in three patients with prostate cancer.
Figure 5B:
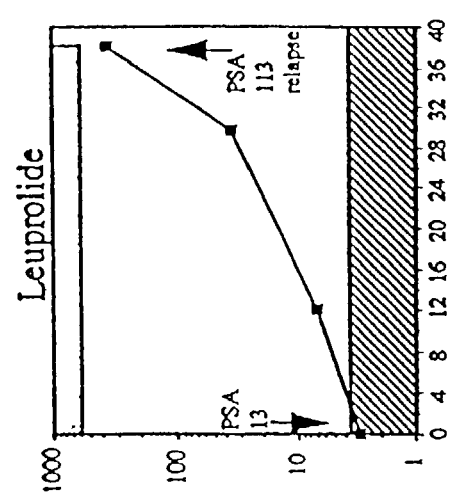
Figure 5A:
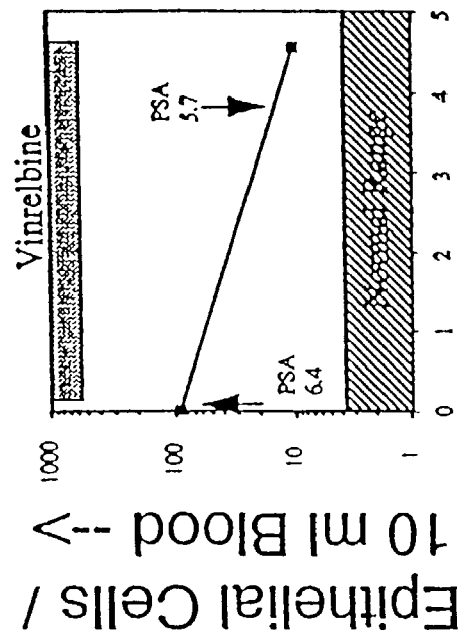

Disease Activity is Correlatable with Number of Circulating Epithelial Cells in Prostate Cancer Patients Three patients with metastatic disease of the prostate were assessed for the presence of circulating epithelial cells in their blood following chemotherapeutic treatment. The results are presented in FIG. 5. The data reveal that an increase in circulating epithelial cells in the blood is correlatable with disease activity. Also in three patients with no detectable spread of the cancer, epithelial cells were found in 20 ml of the peripheral blood (16 cells±4). As shown in Table V, the number of epithelial cells in the blood of prostate cancer patients was statistically different (P less than 0.001) than normal controls.

TABLE V

| Number of Epithelial Cells Per 20 ml Blood | PSA Level (µg/ml) | Gleason Grade |
|---|---|---|
| 4 | 6.0 | 3 + 4 = 7 |
| 12 | 6.5 | 3 + 4 = 7 |
| 12 | 11.2 | 3 + 3 = 6 |
| 16 | 26.0 | 4 + 4 = 8 |
| 20 | | |
| 24 | 5.6 | 3 + 4 = 7 |
| 28 | | |

Control blood samples were obtained from normal individuals, individuals known to have benign tumors and those patients with inflammatory diseases. Based on statistical data, the results reveal that a cut-off point of approximately 6.8 cells per 20 ml of blood was useful as a diagnostic marker for prostate cancer.

EXAMPLE 6

Figure 6:
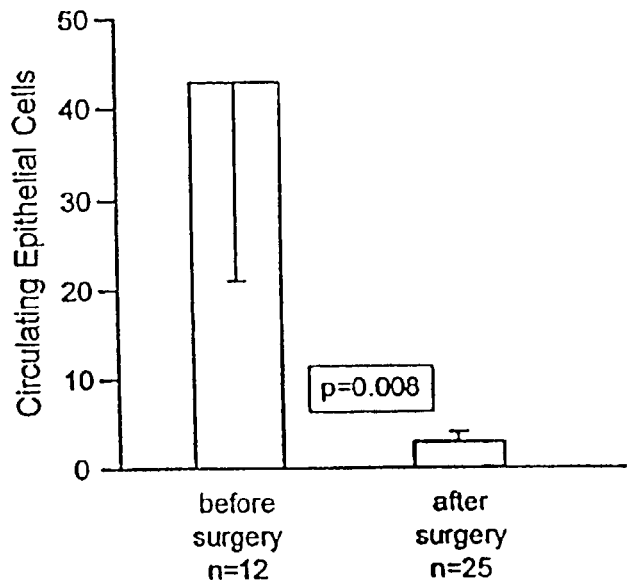
FIG. 6 is a graph which shows that circulating epithelial cell number in patients with colon cancer is significantly decreased after surgical removal of the tumor.

Disease Activity is Correlatable with Number of Circulating Epithelial Cells in Colon Cancer Patients The assay method of the present invention may be used to advantage in the assessment of patients with a variety of different cancer types. To illustrate, the method was also used to assess circulating epithelial levels in patients with colon cancer. Colon cancer patients without evidence of metastases were evaluated for the presence of circulating epithelial cells before and after surgery. The results are shown in FIG. 6 and summarized in Table VI. The data reveal that the number of circulating epithelial cells in colon cancer patients is greater prior to surgical intervention.

TABLE VI

CIRCULATING EPITHELIAL CELLS IN COLON CANCER PATIENTS WITHOUT EVIDENCE OF METASTASES

| TIME OF TESTING | NUMBER OF PATIENTS TESTED | CIRCULATING EPITHELIAL CELLS DETECTED BY FLOW CYTOMETRY IN 10 ml OF BLOOD | |
|---|---|---|---|
| | | MEAN ± SEM | RANGE |
| Before surgery | 12 | 42.3 ± 22.0 | 0-234 |
| After surgery | 25 | 2.7 ± 0.7 | 0-15 |

Figure 7:
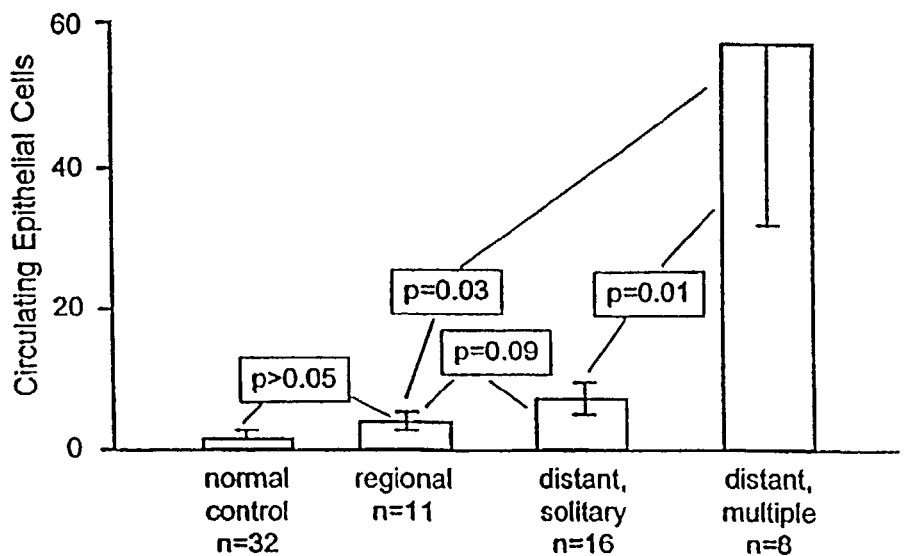
FIG. 7 is a graph which shows that circulating epithelial cell number in patients with metastatic disease of the colon increases with the severity and extent of metastatic disease.
Figure 8:
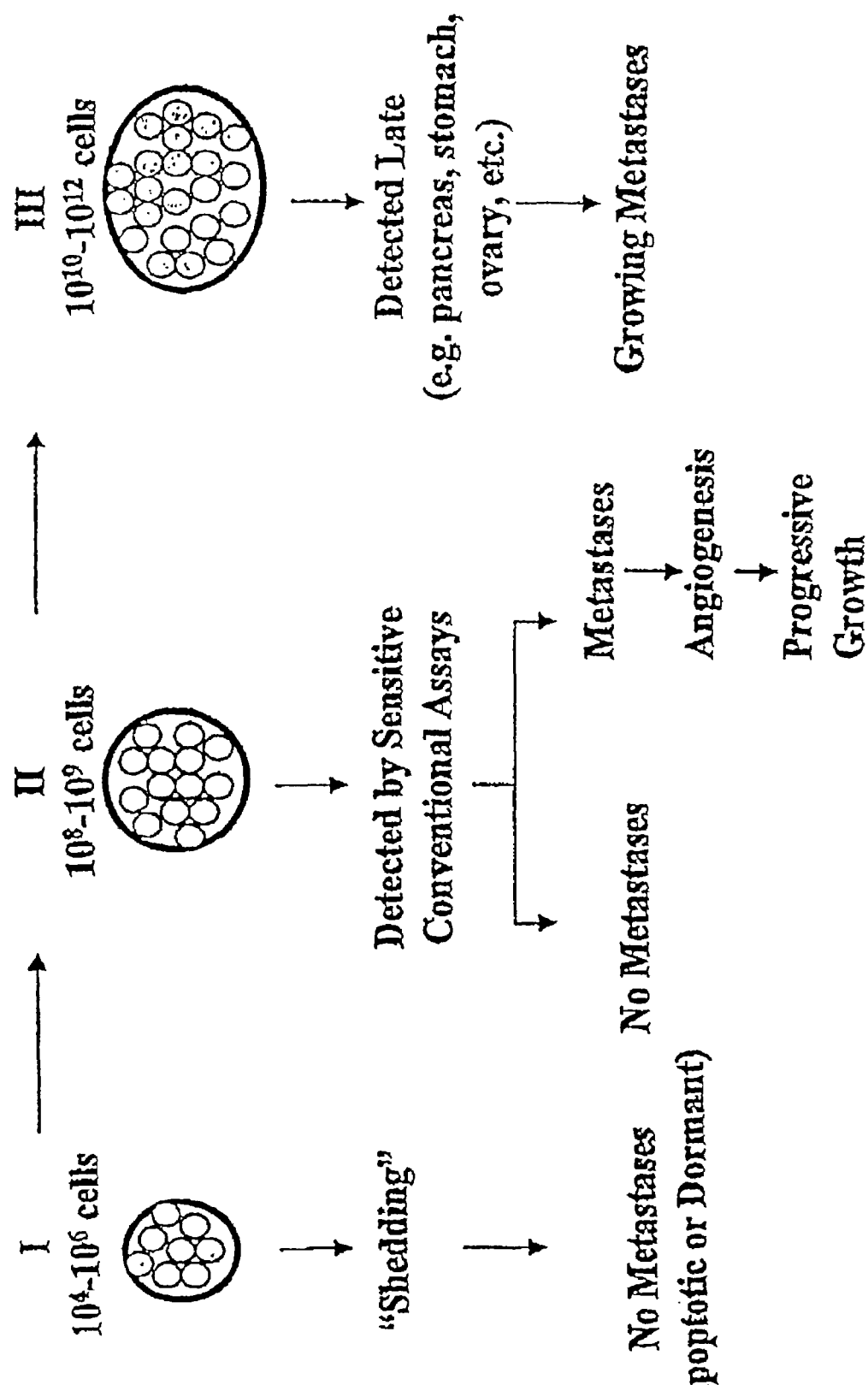
FIG. 8 is a schematic diagram showing the progression of cancer from a primary tumor to growing metastases.

Table VII and FIG. 7 depict data obtained when colon cancer patients with evidence of metastases were assessed for the presence and number of circulating epithelial cells.

The results revealed that the number of epithelial cells in peripheral blood is larger in patients with metastatic disease as compared to local disease after surgery. The results further show that the extent of metastatic disease may be correlated with the number of circulating epithelial cells.

TABLE VII

CIRCULATING EPITHELIAL CELLS IN COLON CANCER PATIENTS WITH EVIDENCE OF METASTASES

| METASTATIC STATUS OF PATIENTS TESTED | NUMBER OF PATIENTS TESTED | CIRCULATING EPITHELIAL CELLS DETECTED BY FLOW CYTOMETRY IN 10 ML OF BLOOD | |
|---|---|---|---|
| | | MEAN ± SD | RANGE |
| REGIONAL | 11 | 3.7 ± 0.6 | 1-6 |
| DISTANT, SOLITARY | 16 | 7.6 ± 2.0 | 0-21 |
| DISTANT, MULTIPLE | 8 | 54.0 ± 25.1 | 5-200 |
| NORMAL CONTROL | 32 | 1.0 ± 0.2 | 0-4 |

The examples above demonstrate the highly significant differences in the number of circulating epithelial cells between healthy individuals and patients with breast, prostate and colon cancer. In addition, significant differences in the number of circulating epithelial cells were found between patients with no detectable spread, spread to local lymph nodes and distant metastasis (Racila et al., (1998), supra). Additionally, the number of epithelial cells in the blood of patients after surgical removal of a primary carcinoma of the breast was monitored over a one-year period. In some of these patients residual disease was detected. See FIG. 7. In patients with metastatic disease, the changes in peripheral blood tumor cell count correlated with the tumor load and response to treatment. The results of these studies reveal the potential of the cell-based assay of the present invention as an objective non-invasive tool to detect the presence of malignant disease and measure the activity of the disease. Cellular morphology and immunophenotype reveal the malignant nature of the isolated cells.

EXAMPLE 7

Tissue Source Identification of Isolated Epithelial Cells

All of the forementioned studies in patients reveal that there is an excess of epithelial cells in patients who have cancer, compared to normal individuals or patients without cancerous diseases, including benign tumors. It is essential, however, to prove that these excess epithelial cells are, in fact, cancer cells. This was accomplished by performing an experiment in which immunomagnetically purified epithelial cells from patients with or without cancer were cytospun onto a glass slide and treated with anti-mucin. In addition, normal epithelial cells which were obtained from foreskin and blood from normal individuals, both used as controls, were also cytospun. It is significant that the slides were coded and examined "blinded", that the observer had training in pathology and that normal epithelial cells were included. As can be seen in FIG. 4, there is a marked difference between the cancer cells versus normal epithelial cells. Normal epithelial cells have a low nuclear to cytoplasmic ratio, i.e., there is abundant cytoplasm and a relatively small nucleus. The nucleus shows a smooth distribution of chromatin. The cells do not stain with anti-mucin. In contrast, cells from two patients with breast cancer have very large nuclei and a small rim of cytoplasm. Additionally, the chromatin is disorganized as shown by the dark patches in the nucleus and the cells stain intensively with anti-mucin. The same is observed in cells from two patients with prostate cancer. A physician trained in pathology was shown coded slides from patients with and without cancer (total of 21 slides). The pathology-trained physician correctly identified bloods from all the controls as not having cancer cells and displayed no-intraobserved error when shown slides twice. In the cases of two patients with prostate cancer, tumor cells were not seen in the study. One slide was re-examined and tumor cells were observed. The cause of this discrepancy appears to be the amount of time spent scanning the cell smear. In summary, the cytomorphology and immunophenotype indicate that the excess epithelial cells present in the blood in patients with cancer are indeed cancer cells.

The experiments described above indicated that the methods disclosed herein enable the detection of cancer cells in the blood of patients with early tumors. Indeed, in 25 of 27 patients who were clinically determined to have organ-confined disease (early stage cancer), we detected the presence of cancer cells in the blood. This means that the assay should detect cancer cells much earlier in those solid tumors that are normally detected late ($10^9$-$10^{10}$ tumor cells). Moreover, the test should allow detection of breast and prostate cancer earlier, perhaps before detection of a primary tumor by conventional means. The organ-origin of tumor cells in the blood for prostate can be established by staining with anti-prostate specific membrane antigen (PMSA), anti-PSA (prostate specific antigen), or other antibodies specific to the prostate in male subjects. For breast carcinoma in female patients, staining with anti-mammoglobin, anti-progesterone receptor, anti-estrogen receptor and anti-milk fat globulin antigen I and II will indicate a breast origin of tumor.

Our test should detect carcinoma cells from other organs, e.g., pancreas, esophagus, colon, stomach, lung, ovary, kidney, etc. The following table shows examples in which excess epithelial cells were observed in several patients with carcinomas other that the breast and prostate.

TABLE VIII

| NUMBER OF CELLS PER 20 ML BLOOD | CANCER DIAGNOSIS |
|---|---|
| 8 | Uterus adenocarcinoma (Stage 1B) |
| 11 | Head and Neck adenocarcinoma |
| 15 | Lung small undifferentiated |
| 14 | Neck Squamous cell carcinoma |

Each of the carcinomas described in the table above express tissue specific antigens whose corresponding antibodies can be used to determine the organ-origin of the circulating tumor cells.

The blood test of the invention can also be used to detect cancer cells in patients previously treated successfully for cancer and now in long term complete remission. Indeed circulating epithelial cells, i.e., dormant tumor cells, have been detected in patients treated five or more years previously and who appear to be clinically free of tumor. This explains why recurrence in patients can occur many years, even decades after apparently successful treatment. In fact, accumulating evidence suggests that the recurrence rate of breast cancer is at slow steady rate 10-12 years after mastectomy.

EXAMPLE 8

Detection of Tumor Cells in the Blood of a Patient with High PSA Levels and a Negative Biopsy As indicated by the foregoing examples, the present invention may be used to advantage to diagnose cancer in presently asymptomatic patients. To illustrate this point, a patient with a two year history of high PSA levels (>12 µg/ml), had a needle biopsy of the prostate performed two weeks prior to the analysis set forth below. The biopsy did not reveal the presence of malignancy. It is also noteworthy that a prior biopsy performed 18 months earlier was also negative.

Before obtaining a 20 ml blood sample, the patient was given a digital rectal exam and a gentle massage of his enlarged prostate with the intention of increasing the occurrence of tumor cells in the blood. The blood sample was enriched using the methods of the present invention. The enriched fraction was examined by microscopy employing a Wrights-Giemsa stain. Morphological examination of the isolated cells revealed their malignant character. Clearly this patient had cancer. Given the high PSA levels observed, a diagnosis of prostate cancer is likely. The origin of the cells may be determined using appropriate reagents as described herein. The results presented in this example reveal that the methods of the present invention can be used to detect cancers which might otherwise go undetected.

The notion of employing a localized massage to promote shedding of tumor cells into blood as a means of enhancing sensitivity of the blood test is a concept with considerable merit. Cells that are released into the circulation by this approach, following isolation may be used for a variety of different purposes. In the case of cells isolated with ferrofluids, isolated cells can be readily cultured and/or cloned. The resultant cell lines can be used to assess a variety of malignant cell characteristics such as chemotherapeutic sensitivity and growth factor dependency.

EXAMPLE 9

Tests Kits for Diagnosing Various Aspects of Cancer.

Also contemplated for use in the present invention are test kits comprising the reagents used to perform the assay of the invention. Such kits are designed for particular applications. Reagents may be assembled to facilitate screening of patients for circulating rare cells, including but not limited to tumor cells. In this embodiment, the kits contain colloidal magnetic particles comprising a magnetic core material, a protein base coating material and a biospecific ligand which binds specifically to a characteristic determinant present on the cancer cell to be isolated. The kit also includes at least one additional biospecific reagent which has affinity for a second characteristic determinant on the cancer cell to be isolated which differs from the determinant recognized by the biospecific ligand. The kit also includes a cell specific dye for excluding non-nucleated cells and other non-target sample components from analysis.

A typical kit according to this invention may include anti-EpCAM coupled directly or indirectly to magnetic nanoparticles, and a pair of monoclonal antibodies, the first antibody recognizing a cancer specific determinant and the second antibody having affinity for a non-tumor cell determinant, e.g., a pan leukocyte antigen. The kit also contains a nucleic acid dye to exclude non-nucleated cells from analysis. The kit of the invention may optionally contain a biological buffer, a permeabilization buffer, a protocol, separation vessels, analysis chamber, positive cells or appropriate beads and an information sheet.

The kits described above may also be produced to facilitate diagnosis and characterization of particular cancer cells detected in circulation. In this embodiment, the kits contain all of the items recited above, yet also preferably contain a panel of cancer specific monoclonal antibodies. Using breast cancer as an example, a kit for diagnosis may contain anti-MUC-1, anti-estrogen, anti-progesterone receptor antibodies, anti-CA27.29, anti-CA15.3, anti-cathepsin D, anti-p53, anti-urokinase type plasminogen activator, anti-epidermal growth factor, anti-epidermal growth factor receptor, anti-BRCA1, anti-BRCA2, anti-prostate specific antigen, anti-plasminogen activator inhibitor, anti-Her2-neu antibodies or a subset of the above.

A kit is also provided for monitoring a patient for recurring disease and/or residual cells following eradication of the tumor. In this embodiment, the type of cancer will already have been diagnosed. Accordingly, the kit will contain all of the reagents utilized for screening biological samples for cancer yet also contain an additional antibody specific for the type of cancer previously diagnosed in the patient. Again using breast cancer as an example such a kit might contain anti-MUC-1. Alternatively, the kit may contain anti-Her2-neu.

The kits of the invention may be customized for screening, diagnosing or monitoring a variety of different cancer types. For example, if the kits were to be utilized to detect prostate cancer, the antibodies included in the kit would be specific for prostate tissue. Suitable antibodies or markers for this purpose include anti-prostate specific antigen, free PSA, prostatic acid phosphatase, creatine kinase, thymosin b-15, p53, HPC1 basic prostate gene and prostate specific membrane antigen. If a patient were to be screened for the presence of colon cancer, an antibody specific for carcinoembryonic antigen (CEA) may be included in the kit. Kits utilized for screening patients with bladder cancer may contain antibodies to nuclear matrix protein (NMP22), Bard Bladder tumor antigen (BTA) or fibrin degradation products (FDP). Markers are known for many different cancer types.

The cells isolated using the kits of the invention may be further studied for morphology, RNA associated with the organ of origin, surface and intracellular proteins, especially those associated with malignancy. Based on existing information on such molecules, it should be possible to determine from their expression on the isolated cell, the metastatic potential of the tumor via analysis of the circulating cells.

It is an object of the invention to provide kits for any cancer for which specific markers are known. A list summarizing those markers known at this time and the usefulness and/or indication follows:

I Indicative of tumor origin
   Muc-1—breast
   PSA, PSMA—prostate
   CEA—colon
   CYPRA 21-1—lung
   CA 125—ovarian
   cytokeratins—see list
   anti-HI67

II Cell cycle
   nucleic acid dye
   cyclin A, C & E
   p27

III Cell viability/apoptosis
   Fas (CD95)
   amexin V
   anti-metalloproteinases IV Drug sensitivity
  estrogen, progesterone & androgen receptors
  HER-2/neu
V. Drug resistance
  P-glycoprotein (MDR)
  t-glutamylcysteine synthase
  taxol-resistance-associated-gene-1-5
  cis-diamminedichloroplatinum II resistance genes
  thymidylate synthetase
  protein kinase C
  telomerase
VI. Staging
  Lewis A
  C
  BRCA-1 BRCA-2
  CA15.3 (Muc-1), CA 27.29, CA 19.9
  LASA
  p53
  cathepsin D
  ras oncogene The following table provides different cytokeratin markers that may be used to assess tissue origin of cells isolated using the methods of the present invention.

The following demonstrates how the practice of the methods of the invention is facilitated by means of a kit for use in detection of circulating breast cancer cells:

As described above, the kit starts with reagents, devices and methodology for enriching tumor cells from whole blood. The kit would contain reagents to test for breast cancer cells in a blood sample which will assess six factors or indicators. The analytical platform needs to be configured such that the reporter molecules DAPi, CY2, CY3, CY3.5, CY5, and CY5.5 will be discriminated by the appropriate excitation and emmission filters. The analytical platform in this example uses a fluorescent microscope equipped with a mercury arc lamp, and the appropriate filter sets for assessing the wavelengths of the detection labels employed. All of the markers are introduced at one time with this method. DAPi, which is excited with UV light, stains nucleic acids, and will be used to determine the nuclear morphology of the cell. CAM 5.2 labelled with CY2 will be used to stain the control cells. CY3 labelled C11 will be used to label cytokeratins 7, 8, 18, and 19. An antibody conjugated with CY3.5 will be used to label HER-2/neu. An antibody conjugated with CY5 will be used to label Muc-1. An antibody conjugated to CY5.5 will be used to label estrogen receptors.

TABLE IX

CYTOKERATIN MARKERS

| Cytokeratin Number | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Adrenal Cortex | − | − | − | − | − | − | − | + | − | − | − | − | − | − | − | − | − | + | + | − |
| Endometrium | − | − | − | − | − | − | + | + | − | − | − | − | − | − | − | − | − | + | + | − |
| Esophagus | − | − | − | + | − | − | − | + | − | − | − | − | + | − | − | − | − | + | + | − |
| Gastro-Intestinal | − | − | − | − | − | − | + | + | − | − | − | − | − | − | − | − | − | + | + | + |
| Kidney | − | − | − | − | − | − | + | + | − | − | − | − | − | − | − | − | + | + | + | − |
| Liver | − | − | − | − | − | − | + | + | − | − | − | − | − | − | − | − | − | + | + | − |
| Lung Columnar | − | − | − | − | − | − | + | + | − | − | − | − | − | − | − | − | − | + | + | + |
| Lung Basal | − | − | − | − | + | − | − | − | − | − | − | − | − | + | + | − | + | − | − | − |
| Mammary Gland Luminal | − | − | − | − | − | − | + | + | − | − | − | − | − | − | − | − | − | + | + | − |
| Mammary Gland Basal | − | − | − | − | + | − | − | − | − | − | − | − | − | + | − | − | + | − | − | − |
| Mesothelium | − | − | − | − | − | + | − | + | + | − | − | − | − | − | − | − | − | + | + | − |
| Oral | − | − | − | − | − | − | − | − | − | − | − | − | − | − | − | − | + | − | − | − |
| Ovary | − | − | − | − | − | − | + | + | − | − | − | − | − | − | − | − | − | + | + | − |
| Pancreas | − | − | − | + | + | − | + | + | − | − | − | − | + | − | − | + | + | + | + | − |
| Pituitary Endocrine cells | − | − | − | − | − | − | − | + | − | − | − | − | − | − | − | − | − | + | − | − |
| Pituitary Follicular cells | − | − | − | − | − | − | + | − | − | − | − | − | − | − | − | − | − | − | + | − |
| Prostate Basal | − | − | − | − | + | + | − | + | − | + | − | + | + | − | − | + | + | + | − |
| Prostate Luminal | − | − | − | − | − | − | − | + | − | − | − | − | − | − | − | − | − | + | + | − |
| Skin | − | − | − | − | − | − | − | − | − | − | − | − | − | − | − | − | − | − | − | − |
| Testis | − | − | − | − | − | − | − | + | − | − | − | − | − | − | − | − | − | + | − | − |
| Thymus | − | − | − | − | + | − | − | − | − | + | − | − | − | − | − | − | − | + | − | + |
| Thyroid | − | − | − | + | − | − | + | − | + | − | − | + | − | − | − | − | − | + | + | − |
| Urinary Bladder | − | − | − | + | + | − | + | + | − | − | − | + | − | − | − | − | − | + | − | + |
| Uterine Cervix | − | − | − | − | + | + | + | + | − | − | − | − | − | + | + | + | + | + | + | − |
| Non-Epithelial: | | | | | | | | | | | | | | | | | | | | |
| Mammary adenocarcinoma | − | − | − | − | − | − | + | + | − | − | − | − | − | − | − | − | − | + | + | − |
| Prostate adenocarcinoma | − | − | − | − | − | − | + | + | − | − | − | − | − | − | − | − | − | + | + | − |
| Pancreatic adenocarcinoma | − | − | − | − | − | − | + | + | − | − | − | − | − | − | − | − | − | + | + | + |
| Gastro-Intestinal adenocarcinoma | − | − | − | − | − | − | + | + | − | − | − | − | − | − | − | − | − | + | + | + |
| Endometrium adenocarcinoma | − | − | − | − | − | − | + | + | − | − | − | − | − | − | − | − | − | + | + | − |
| Lung adenocarcinoma | − | − | − | − | − | − | + | + | − | − | − | − | − | − | − | − | − | + | + | − |
| Lung SCC | − | − | − | + | − | − | − | + | − | − | − | + | + | + | + | + | + | − | − | − |
| Liver | − | − | − | − | − | − | + | + | − | − | − | − | − | − | − | − | − | + | + | − |
| Kidney renal cell tumor | − | − | − | − | − | − | + | + | − | − | − | − | − | − | − | − | + | + | + | − |
| Oral SCC | − | − | + | + | − | + | − | − | − | + | − | + | − | − | − | + | + | − | − | + |
| Ovary | − | − | − | + | + | − | + | + | − | + | − | + | − | − | − | − | − | + | + | − |
| Pituitary adenoma | − | − | − | − | − | − | − | + | − | − | − | − | − | − | − | − | − | + | − | − |
| Testis | − | − | − | − | − | − | − | + | − | − | − | − | − | − | − | − | − | + | + | − |
| Thyroid | − | − | − | − | + | − | − | + | − | + | − | + | − | − | − | − | − | + | + | − |
| Urinary Bladder | − | − | − | − | − | − | + | − | − | − | − | − | + | − | − | − | − | − | − | + |
| Uterine cervix | − | − | − | − | − | − | + | + | − | − | − | − | − | + | − | + | + | + | − |
| Valvular carcinoma | − | − | − | − | − | − | − | − | + | − | + | + | − | − | − | − | − | − | − |

By using the appropriate excitation and emmission filters, the cancer cells will be identified.

Examples of different types of cancer that may be detected using the compositions, methods and kits of the present invention include apudoma, choristoma, branchioma, malignant carcinoid syndrome, carcinoid heart disease, carcinoma e.g., Walker, basal cell, basosquamous, Brown-Pearce, ductal, Ehrlich tumor, in situ, Krebs 2, merkel cell, mucinous, non-small cell lung, oat cell, papillary, scirrhous, bronchiolar, bronchogenic, squamous cell and transitional cell reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, mesenchymoma, mesonephroma, myosarcoma, ameloblastoma, cementoma, odontoma, teratoma, throphoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, leydig cell tumor, papilloma, sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, antiokeratoma, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (Kaposi's, and mast-cell), neoplasms (e.g., bone, digestive system, colorectal, liver, pancreatic, pituitary, testicular, orbital, head and neck, central nervous system, acoustic, pelvic, respiratory tract, and urogenital), neurofibromatosis, and cervical dysplasia.

The present invention is not limited to the detection of circulating epithelial cells only. Endothelial cells have been observed in the blood of patients having a myocardial infarction. Endothelial cells, myocardial cells, and virally infected cells, like epithelial cells, have cell type specific determinants recognized by available monoclonal antibodies. Accordingly, the methods and the kits of the invention may be adapted to detect such circulating endothelial cells. Additionally, the invention allows for the detection of bacterial cell load in the peripheral blood of patients with infectious disease, who may also be assessed using the compositions, methods and kits of the invention.

Several citations to journal articles, US Patents and US Patent applications are provided hereinabove. The subject matter of each of the foregoing citations is incorporated by reference in the present specification as though set forth herein in full.

While certain of the preferred embodiments of the present invention have been described and specifically exemplified above, it is not intended that the invention be limited to such embodiments. Various modifications may be made thereto without departing from the spirit of the present invention, the full scope of which is delineated in the following claims.

What is claimed is:

1. A coated magnetic particle comprising a nanoparticle core material of magnetite, a protein base coating material of bovine serum albumin directly coated onto quasi-stable crystalline clusters of said core material and an additional streptavidin coating coupled to said base coating material, wherein a fraction of the streptavidin which is coupled to said base coating material is bound to biotinylated antibody and substantial portion of said streptavidin remaining is bound to biotin-bovine serum albumin conjugate.

2. A composition comprising a plurality of magnetic particles as claimed in claim 1, suspended in a biologically compatible aqueous medium.

3. A coated, magnetic particle within a population of coated, magnetic nanoparticles, said coated, magnetic particle comprising:
   a. a fractionated nanoparticle core between 90 nm and 150 nm that provides between 83% and 93% target recovery in external magnetic gradient wherein said core comprises at least one transition metal oxide;
   b. a base coating material adsorbed onto said nanoparticle core wherein said material comprises a protein directly coated onto a quasi-stable crystalline cluster of said fractionated nanoparticle core; and
   c. an additional streptavidin coating coupled to said base coating material, wherein a fraction of the streptavidin which is coupled to said base coating material is bound to biotinylated antibody and substantial portion of said streptavidin remaining is bound to biotin-bovine serum albumin conjugate.

4. A coated magnetic particle comprising a nanoparticle core material having a magnetic transition metal oxide core, a protein base coating material coated on the nanoparticle core and an additional streptavidin coating coupled to said base coating material through a bifunctional linking compound, wherein a fraction of the streptavidin which is coupled to said base coating material is bound to biotinylated antibody and substantial portion of said streptavidin remaining is bound to biotin-bovine serum albumin conjugate.

5. The coated magnetic particle of claim 4 wherein said bifunctional compound is succinimidyl-propiono-dithiopyridine or sulfosuccinimidil-4-[maleimidomethyl]cyclohexane-1-carboxylate.

6. The coated magnetic particle of claim 4 wherein said magnetic transition metal oxide core is magnetite.

* * * * *